United States Patent
Friedman et al.

(10) Patent No.: US 9,198,683 B2
(45) Date of Patent: Dec. 1, 2015

(54) TISSUE CAPTURE AND OCCLUSION SYSTEMS AND METHODS

(75) Inventors: Paul A. Friedman, Rochester, MN (US); Charles J. Bruce, Rochester, MN (US); Samuel J. Asirvatham, Rochester, MN (US); Trevor A. McCaw, Vancouver (CA); Elliot Y. K. Hong, Vancouver (CA)

(73) Assignees: AEGIS MEDICAL INNOVATIONS, INC., Vancouver, B.C. (CA); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 420 days.

(21) Appl. No.: 13/499,397

(22) PCT Filed: Sep. 30, 2010

(86) PCT No.: PCT/US2010/050833
§ 371 (c)(1),
(2), (4) Date: Jul. 11, 2012

(87) PCT Pub. No.: WO2011/041488
PCT Pub. Date: Apr. 7, 2011

(65) Prior Publication Data
US 2012/0330351 A1     Dec. 27, 2012

Related U.S. Application Data

(60) Provisional application No. 61/247,248, filed on Sep. 30, 2009.

(51) Int. Cl.
*A61B 17/00*     (2006.01)
*A61B 17/29*     (2006.01)
(Continued)

(52) U.S. Cl.
CPC .......... *A61B 17/29* (2013.01); *A61B 17/12013* (2013.01); *A61B 5/0402* (2013.01);
(Continued)

(58) Field of Classification Search
CPC ......................... A61B 17/29; A61B 17/12013
USPC ......................................................... 606/205
See application file for complete search history.

(56) References Cited

U.S. PATENT DOCUMENTS

| 4,041,952 A | 8/1977 | Morrison, Jr. et al. |
| 5,026,370 A | 6/1991 | Lottick |

(Continued)

FOREIGN PATENT DOCUMENTS

| WO | 2008/036408 A2 | 3/2008 |
| WO | 2008/036408 A3 | 9/2008 |
| WO | 2009/120953 A2 | 10/2009 |

OTHER PUBLICATIONS

International Search Report issued Jun. 15, 2011, in Korea, Patent Application No. PCT/US2010/050833, filed Sep. 30, 2010.
(Continued)

*Primary Examiner* — Brian Szmal
(74) *Attorney, Agent, or Firm* — Mueting, Raasch & Gebhart, P.A.

(57) ABSTRACT

Systems and methods capture and/or occlusion of selected body tissue using various tissue characteristics and/or techniques are described. In the context of left atrial appendage closure, the systems and methods can be used to capture the left atrial appendage while a closure instrument (suture, clip, ring, etc.) is placed over the appendage and tightened down or a closure method (ablation, cryogenic procedures, stapling, etc.) is performed to close the left atrial appendage.

20 Claims, 16 Drawing Sheets

(51) Int. Cl.
*A61B 17/12* (2006.01)
*A61B 5/0402* (2006.01)
*A61B 17/30* (2006.01)
*A61B 19/00* (2006.01)

(52) U.S. Cl.
CPC .............. *A61B2017/00026* (2013.01); *A61B 2017/00243* (2013.01); *A61B 2017/2926* (2013.01); *A61B 2017/308* (2013.01); *A61B 2019/465* (2013.01)

(56) References Cited

U.S. PATENT DOCUMENTS

| | | | |
|---|---|---|---|
| 5,306,234 A | | 4/1994 | Johnson |
| 5,318,589 A | | 6/1994 | Lichtman |
| 5,403,331 A | | 4/1995 | Chesterfield et al. |
| 5,713,896 A | * | 2/1998 | Nardella ................. 606/50 |
| 5,755,717 A | | 5/1998 | Yates et al. |
| 5,865,791 A | | 2/1999 | Whayne et al. |
| 5,957,863 A | | 9/1999 | Koblish et al. |
| 6,068,629 A | | 5/2000 | Haissaguerre et al. |
| 6,120,496 A | | 9/2000 | Whayne et al. |
| 6,206,827 B1 | | 3/2001 | Chin et al. |
| 6,261,242 B1 | | 7/2001 | Roberts et al. |
| 6,488,689 B1 | | 12/2002 | Kaplan et al. |
| 6,666,861 B1 | | 12/2003 | Grabeck |
| 6,669,687 B1 | | 12/2003 | Saadat |
| 6,743,225 B2 | | 6/2004 | Sanchez et al. |
| 6,771,996 B2 | | 8/2004 | Bowe et al. |
| 6,786,905 B2 | | 9/2004 | Swanson et al. |
| 6,887,240 B1 | | 5/2005 | Lands et al. |
| 6,899,710 B2 | | 5/2005 | Hooven |
| 6,932,811 B2 | | 8/2005 | Hooven et al. |
| 7,141,057 B2 | | 11/2006 | Burbank et al. |
| 7,214,180 B2 | | 5/2007 | Chin |
| 7,226,458 B2 | | 6/2007 | Kaplan et al. |
| 7,276,235 B2 | | 10/2007 | Metzner et al. |
| 7,338,434 B1 | | 3/2008 | Haarstad et al. |
| 7,347,856 B2 | | 3/2008 | Wittenberger et al. |
| 7,398,781 B1 | | 7/2008 | Chin |
| 7,468,061 B2 | | 12/2008 | Hooven et al. |
| 7,527,634 B2 | | 5/2009 | Zenati et al. |
| 7,697,972 B2 | | 4/2010 | Verard et al. |
| 7,828,810 B2 | | 11/2010 | Liddicoat et al. |
| 7,846,168 B2 | | 12/2010 | Liddicoat et al. |
| 7,918,865 B2 | | 4/2011 | Liddicoat et al. |
| 7,938,823 B2 | | 5/2011 | Wittenberger et al. |
| 8,628,522 B2 | | 1/2014 | Ibrahim et al. |
| 2002/0151889 A1 | | 10/2002 | Swanson et al. |
| 2002/0177765 A1 | | 11/2002 | Bowe et al. |
| 2003/0163128 A1 | | 8/2003 | Patil et al. |
| 2004/0015163 A1 | * | 1/2004 | Buysse et al. ................. 606/34 |
| 2004/0030335 A1 | | 2/2004 | Zenati et al. |
| 2004/0044340 A1 | | 3/2004 | Francischelli et al. |
| 2004/0064138 A1 | | 4/2004 | Grabek |
| 2004/0097805 A1 | | 5/2004 | Verard et al. |
| 2004/0102804 A1 | | 5/2004 | Chin |
| 2005/0090728 A1 | | 4/2005 | Mest |
| 2005/0154404 A1 | | 7/2005 | Liddicoat et al. |
| 2006/0253129 A1 | | 11/2006 | Liddicoat et al. |
| 2006/0271038 A1 | * | 11/2006 | Johnson et al. ................. 606/45 |
| 2007/0073313 A1 | | 3/2007 | Liddicoat et al. |
| 2007/0164900 A1 | | 7/2007 | Schneider et al. |
| 2008/0033457 A1 | | 2/2008 | Francischelli et al. |
| 2008/0058657 A1 | | 3/2008 | Schwartz et al. |
| 2008/0058845 A1 | | 3/2008 | Shimizu et al. |
| 2008/0097139 A1 | | 4/2008 | Clerc et al. |
| 2008/0125795 A1 | | 5/2008 | Kaplan et al. |
| 2008/0147097 A1 | | 6/2008 | Liddicoat et al. |
| 2008/0172052 A1 | | 7/2008 | Eder et al. |
| 2008/0221593 A1 | | 9/2008 | Liddicoat et al. |
| 2008/0243183 A1 | | 10/2008 | Miller et al. |
| 2008/0255470 A1 | | 10/2008 | Hauck et al. |
| 2008/0294175 A1 | | 11/2008 | Bardsley et al. |
| 2009/0036881 A1 | | 2/2009 | Artale et al. |
| 2009/0143791 A1 | | 6/2009 | Miller et al. |
| 2009/0157118 A1 | | 6/2009 | Miller et al. |
| 2010/0069925 A1 | | 3/2010 | Friedman et al. |
| 2011/0112569 A1 | | 5/2011 | Friedman et al. |
| 2012/0327204 A1 | | 12/2012 | Friedman et al. |

OTHER PUBLICATIONS

Written Opinion issued Jun. 15, 2011, in Korea, Patent Application No. PCT/US2010/050833, filed Sep. 30, 2010.
International Preliminary Report on Patentability issued Apr. 3, 2012, in Switzerland, Patent Application No. PCT/US2010/050833, filed Sep. 30, 2010.

* cited by examiner

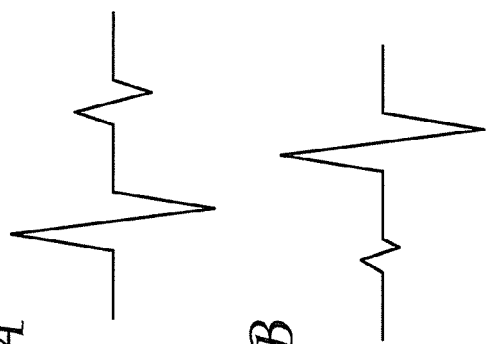
Fig. 8A
Fig. 8B
Fig. 7
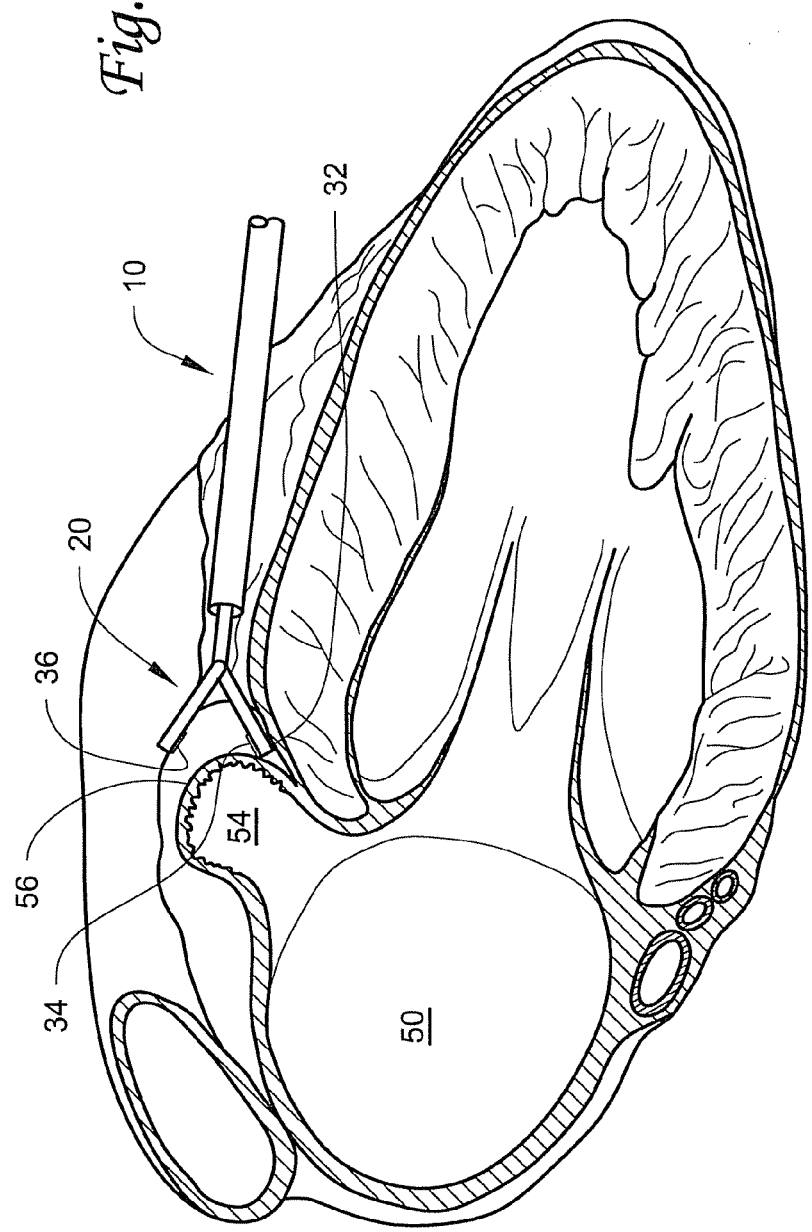

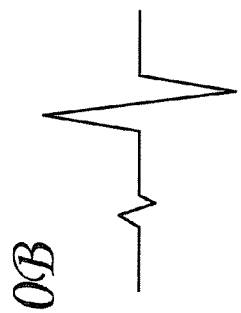
Fig. 9
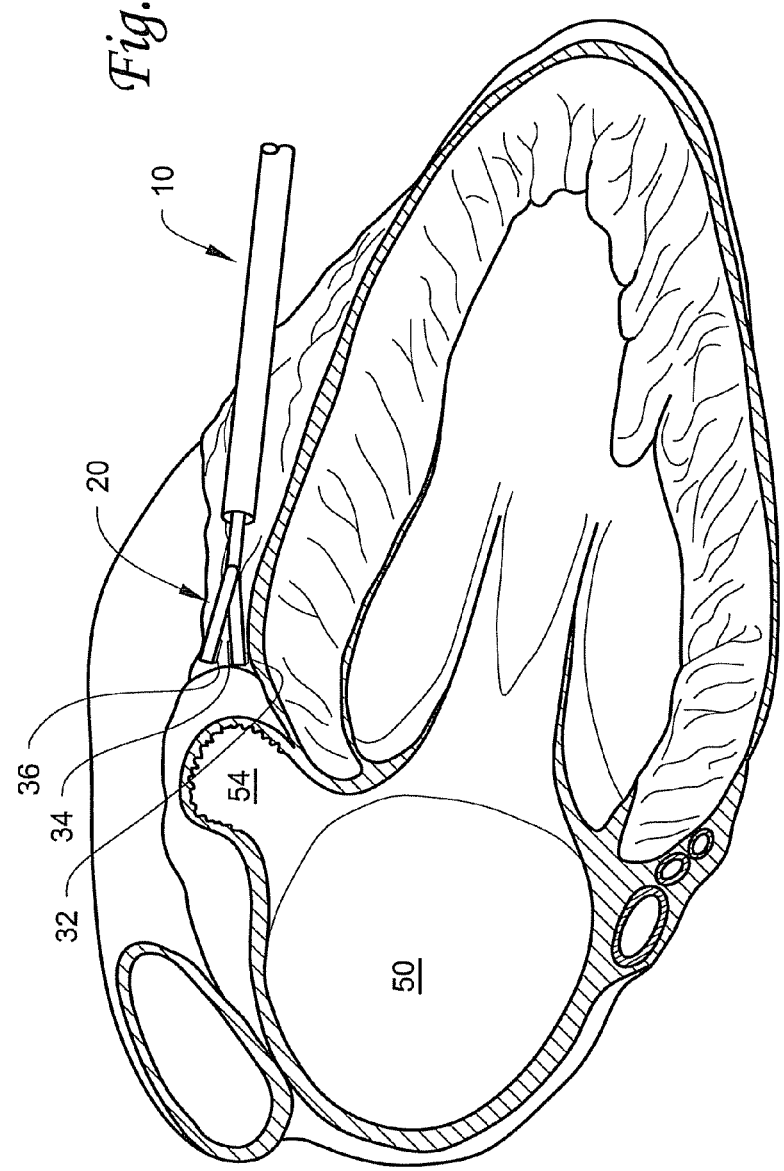
Fig. 10A
Fig. 10B

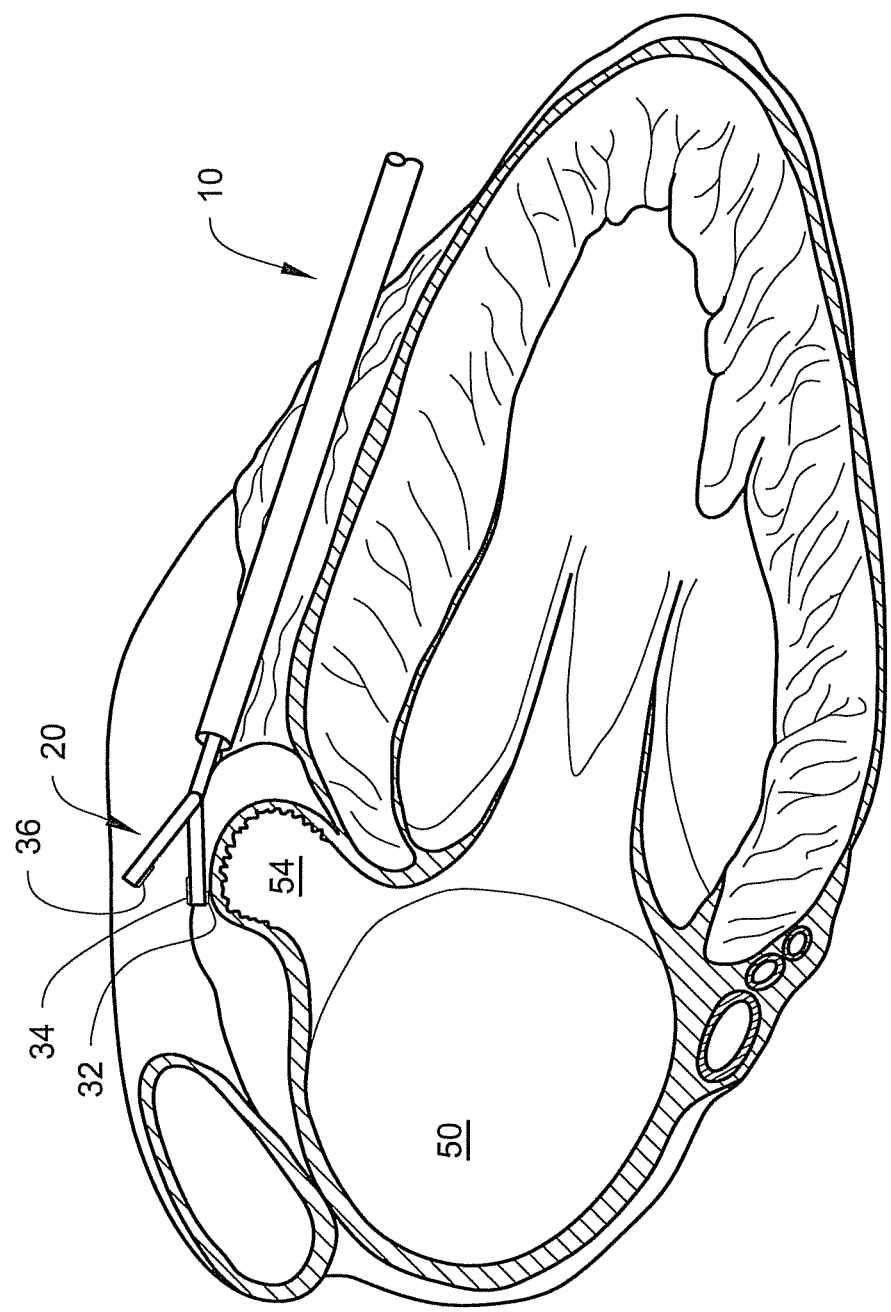

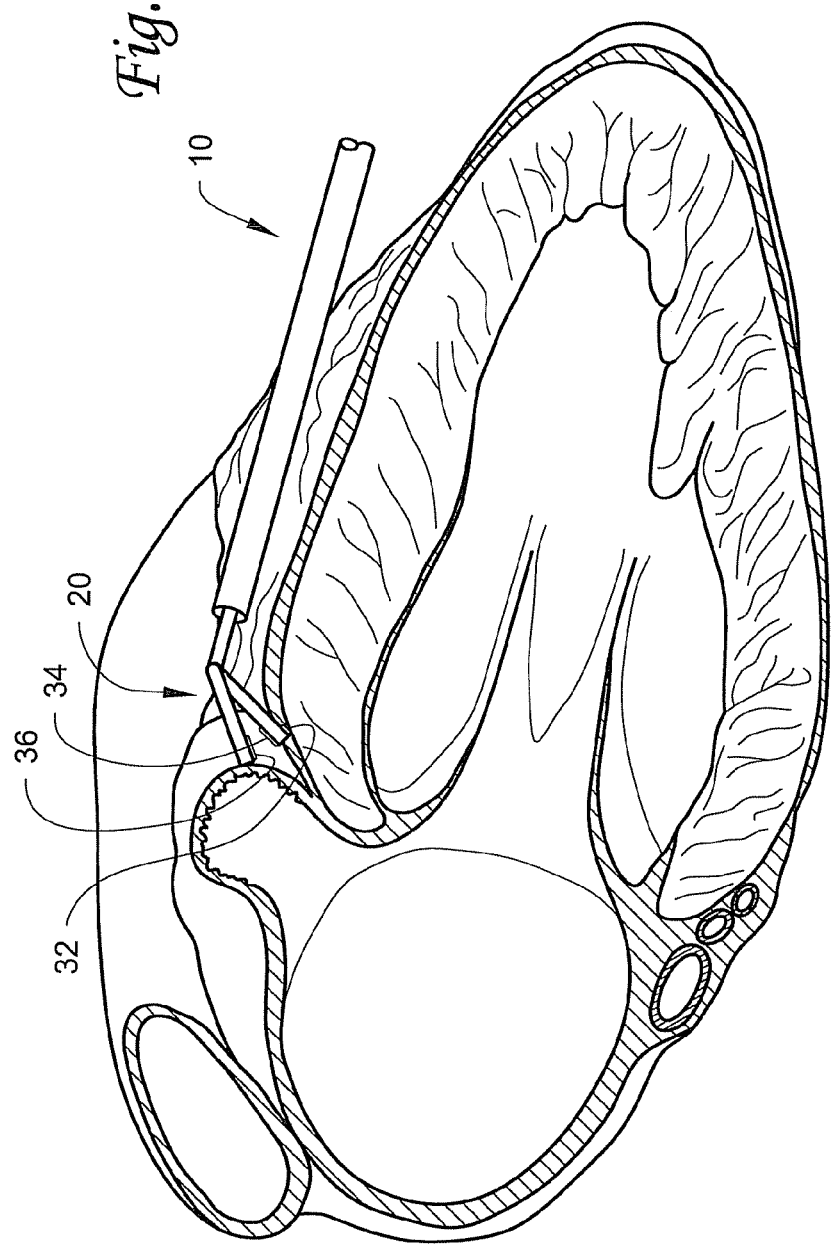
*Fig. 12*
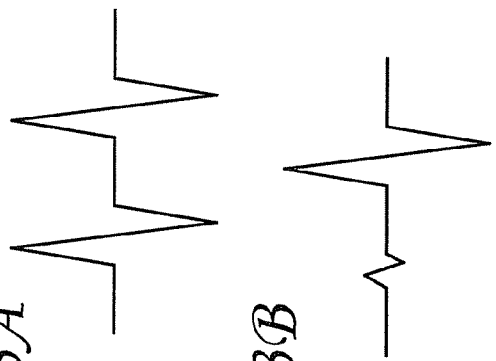
*Fig. 13A*
*Fig. 13B*

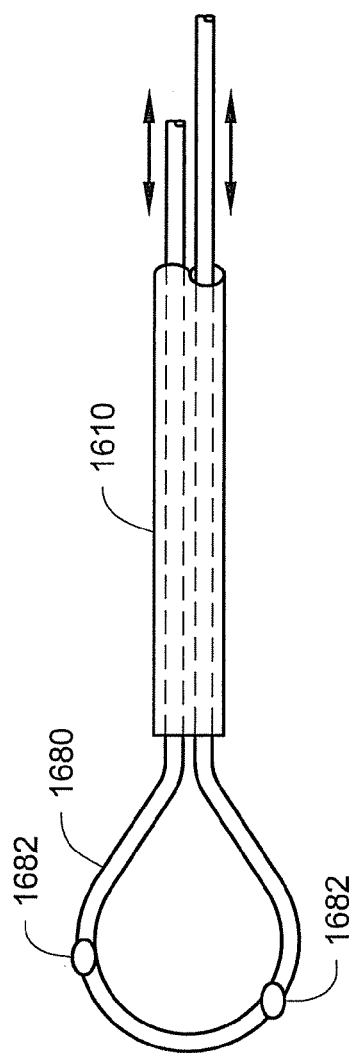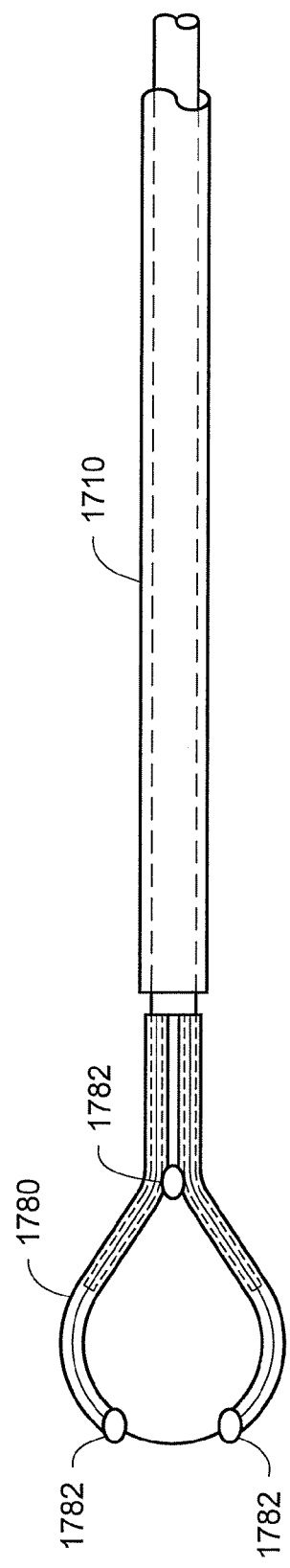
Fig. 26
Fig. 27

TISSUE CAPTURE AND OCCLUSION
SYSTEMS AND METHODS

RELATED APPLICATIONS

This application is a U.S National Stage Application of International Application No. PCT/US2010/050833, titled TISSUE CAPTURE AND OCCLUSION SYSTEM AND METHODS, filed on 30 Sep. 2010, published in the English language on 7 Apr. 2011, as International Publication No. WO 2011/041488 A2, which claims the benefit under 35 U.S.C. §119 of U.S. Provisional Application Ser. No. 61/247,248 filed 30 Sep. 2009, entitled TISSUE CAPTURE AND OCCLUSION SYSTEMS AND METHODS, which is incorporated herein by reference in its entirety.

Systems and methods for capturing and/or occluding selected tissue within the internal body of a patient using various techniques are described herein.

Atrial fibrillation is a common cardiac rhythm disorder affecting a population of approximately 2.5 million patients in the United States alone. Atrial fibrillation results from a number of different causes and is characterized by a rapid chaotic heart beat. In addition to the risks associated with a disordered heart beat, patients with atrial fibrillation also have an increased risk of stroke. It has been estimated that approximately 75,000-90,000 atrial fibrillation patients in the United States each year suffer a stroke related to that condition. It appears that strokes in these patients result from emboli many of which may originate from the left atrial appendage. The irregular heart beat causes blood to pool in the left atrial appendage, allowing clots to accumulate over time. From time to time, a clot may dislodge from the left atrial appendage and may enter the cranial circulation causing a stroke, the coronary circulation causing a myocardial infarction, the peripheral circulation causing limb ischemia, as well as other vascular beds.

Significant efforts have been made to reduce the risk of stroke in patients suffering from atrial fibrillation. Most commonly, those patients are treated with blood thinning agents, such as Coumadin, to reduce the risk of clot formation. While such treatment can significantly reduce the risk of stroke, it also increases the risk of bleeding and for that reason is inappropriate for many atrial fibrillation patients.

As an alternative to drug therapy, minimally invasive surgical procedures for closing the left atrial appendage have been proposed. Most commonly, the left atrial appendage has been closed or removed concurrently with open surgical procedures, typically where the heart has stopped and the chest opened through the sternum. Because of the significant risk and trauma of such procedures, left atrial appendage removal occurs almost exclusively when the patient's chest is opened for other procedures, such as coronary artery bypass or valve surgery.

For that reason, alternative procedures which do not require opening of the patient's chest, i.e., a large median sternotomy, have been proposed. U.S. Pat. No. 5,306,234 to Johnson describes a thoracoscopic procedure where access to the pericardial space over the heart is achieved using a pair of intercostal penetrations (i.e., penetrations between the patients ribs) to establish both visual and surgical access. While such procedures may be performed while the heart remains beating, they still require deflation of the patient's lung and that the patient be placed under full anesthesia. Furthermore, placement of a chest tube is typically required to re-inflate the lung, often requiring a hospitalization for a couple of days.

U.S. Pat. No. 5,865,791, to Whayne et al. describes a transvascular approach for closing the left atrial appendage. Access is gained via the venous system, typically through a femoral vein, a right internal jugular vein, or a subclavian vein, where a catheter is advanced in an antegrade direction to the right atrium. The intra-atrial septum is then penetrated, and the catheter passed into the left atrium. The catheter is then positioned in the vicinity of the left atrial appendage which is then fused closed, e.g., using radiofrequency energy, other electrical energy, thermal energy, surgical adhesives, or the like. Whayne et al. further describes a thoracoscopic procedure where the pericardium is penetrated through the rib cage and a lasso placed to tie off the neck of the left atrial appendage. Other fixation means described include sutures, staples, shape memory wires, biocompatible adhesives, tissue ablation, and the like. The transvascular approach suggested by Whayne et al. is advantageous in that it avoids the need to penetrate the patient's chest but suffers from the need to penetrate the intra-atrial septum, may not provide definitive closure, requires entry into the left atrial appendage which may dislodge clot and requires injury to the endocardial surface which may promote thrombus formation. A thoracoscopic approach which is also suggested by Whayne et al. suffers from the same problems as the thoracoscopic approach suggested by Johnson.

Some improved and alternative methods and procedures for performing minimally invasive closure of the left atrial appendage are discussed in, e.g., U.S. Provisional Patent Application No. 60/826,413 filed on 21 Sep. 2006, as well as in International Publication WO 2008/036408 A2, titled DEVICES AND METHODS FOR LIGATING ANATOMICAL STRUCTURES.

These methods and procedures may preferably be capable of being performed on patients who have received only local or general anesthetic, whose hearts have not been stopped, and whose lungs are not deflated. It would be further desirable to provide methods and procedures which approach the left atrial appendage without the need to perform a thoracotomy (opening of the thorax) or the need to perform a transeptal penetration and/or perform the procedure within the left atrium or left atrial appendage. More specifically, it would be preferable to provide methods and procedures which permitted access to the pericardial space from the xiphoid region of a patient's chest.

Closure of the left atrial appendage using a percutaneous approach typically requires devices and techniques that can create a viable working space in the pericardium and provide for direct visualization of the left atrial appendage within that space. The pericardial sac is, however, very slippery, often contains fluid and is under constant motion. These factors make creating a viable working space for direct visualization difficult. Existing technologies are cumbersome (larger, non-steerable, two operator) and potentially traumatic to the cardiac arteries and veins on the epicardial surface. Unintentional trauma to a cardiac artery could cause ischemia or perforations with potentially fatal outcomes for the patient.

Direct visualization, however, requires overcoming a number of technical hurdles including creating a working space in the pericardial space to create a field of view for a videoscope or fiberscope a, removing fluids (blood) that can contaminate/obscure the lens, miniaturizing the tools to be as atraumatic as possible, confirming capture and/or ligations of the selected body tissue, etc. Unfortunately the intravascular tools also have significant drawbacks including the risks and complications of requiring a second percutaneous intravascular access point, a transseptal puncture, causing endocardial trauma (potentially pro-thrombotic), and introducing contrast agents into the circulatory system of patients.

SUMMARY

Systems and methods for capture and/or occlusion (e.g., through ligation) of selected body tissue using various characteristics such as the innate electrical activity, electrical impedance, or other characteristics of the selected body tissue and/or other tissue and/or various techniques, e.g., including force-limiting apparatus, pulse oximetry, etc. are described herein.

In the context of left atrial appendage closure, the systems and methods can be used to capture the left atrial appendage, e.g., while a closure instrument (suture, clip, ring, etc.) is placed over the appendage and tightened down or a closure method (ablation, cryogenic procedures, stapling, etc.) is performed to close the left atrial appendage. As discussed herein, the use of electrical activity (e.g., cardiac electrical activity, impedances through body tissue, etc.) may be used to capture and/or to occlude the left atrial appendage and/or other body tissue. Further, the use of other characteristics (e.g., pulse oximetry, movement, etc.) may be used to capture and/or to occlude the left atrial appendage and/or other body tissue. Still further, additional devices may be used to capture and/or occlude the left atrial appendage, such as, e.g., one or more actuation apparatuses operably coupled to a capture device and/or a ligation device, one or more force-limiting apparatuses operably coupled to a capture device and/or a ligation device.

The systems and methods described herein may preferably be used in connection with minimally invasive surgical techniques (e.g., percutaneous, laparascopic, endoscopic, etc.) in which it can be difficult to visualize the working field and/or where the available working space is limited. One example of such a situation is demonstrated by techniques that require capture and/or occlusion within the pericardial space to, e.g., close the left atrial appendage.

Although described in the context of left atrial appendage capture, the systems and methods described herein may be used in any internal body location where innate electrical activity and/or other characteristics may be used to assist in body tissue capture and/or occlusion. Other body tissues with which the systems and methods described herein could potentially be used may include, e.g., the gastrointestinal tract, central and/or peripheral nervous systems, skeletal muscle groups, etc. As a result, although the embodiments discussed herein are focused on cardiac tissues, use in connection with other body tissues is possible.

With respect to systems and devices for capturing the left atrial appendage, the capture may be accomplished by monitoring cardiac electrical activity using one or more electrodes attached to one or more components of the systems. For example, an impedance monitored across the left atrial appendage, e.g., by electrodes located on a capture device, may change in accordance with the amount of force applied by the capture device and/or ligation device. As a result, a user can determine whether the left atrial appendage has been captured and/or ligated based on the monitored impedance using the systems and methods described herein.

The systems and methods may preferably facilitate minimally invasive surgical navigation to the left atrial appendage (or other anatomy with sufficiently electrically active tissue) through a small incision or needle-stick access. The devices described herein may preferably be delivered through an introducer and sheath (that is possibly curved, steerable and/or deflectable). After access to the pericardial space has been obtained, a guidewire may be placed in the pericardial space to help guide the devices further into the pericardial space. The access needle, introducer sheath, or guidewire may optionally include electrodes that could be used to assist with navigation to a desired location.

Each device described in connection with the systems and methods could potentially be delivered through such a sheath and into the pericardial sac. Although this technology could be used with a wide variety of surgical techniques, it may be well-suited for minimally invasive catheter based procedures. Rather than passing through the rib cage, as with some thoracoscopic techniques, the systems and methods described herein may, for example, rely on a "sub-xiphoid" approach where the percutaneous penetration is first made beneath the rib cage (preferably between the xiphoid and adjacent costal cartilage) and the device is advanced through the penetration, over the epicardial surface (in the pericardial space) to reach a location adjacent to the exterior of the left atrial appendage. Although a sub-xyphoid approach may be used, any intrapericardial access may alternatively be used regardless of the method of entry.

In some embodiments, the systems described herein include a capture device configured to capture body tissue; a capture shaft comprising an elongated body comprising a proximal end and a distal end, wherein the distal end of the capture shaft is coupled to the capture device; a first capture device electrode coupled to the capture device; a second capture device electrode coupled to the capture device; and electrical monitoring apparatus operably coupled to the first capture device electrode and the second capture device electrode. The electrical monitoring apparatus is configured to: monitor an impedance between the first capture device electrode and the second capture device electrode; and determine whether the capture device is proximate a selected tissue based on the monitored impedance.

In various embodiments, the systems described herein may include a capture device that comprises a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration. In some embodiments, the first capture device electrode may be coupled to the interior surface of the first jaw and the second capture device electrode may be coupled to the interior surface of the second jaw. In some embodiments, the first capture device electrode is coupled to the interior surface of the first jaw and the interior surface of the second jaw is free of any electrodes.

In various embodiments, the systems described herein may include force-limiting apparatus operably coupled to the capture device to restrict the amount of force applied by the capture device to the body tissue, wherein the electrical monitoring apparatus is further operably coupled to the force-limiting apparatus and is further configured to use the force-limiting apparatus to restrict the amount of force applied by the capture device based on the monitored impedance.

In various embodiments, the systems described herein, the electrical monitoring apparatus is further configured to monitor the impedance between the first capture device electrode and the second capture device electrode by monitoring the impedance at a selected frequency between the first capture device electrode and the second capture device electrode.

In various embodiments, the systems described herein, the electrical monitoring apparatus is further configured to monitor the impedance between the first capture device electrode and the second capture device electrode by monitoring the impedance at a selected amplitude between the first capture device electrode and the second capture device electrode.

In various embodiments, the systems described herein, the electrical monitoring apparatus is configured to determine whether the capture device is proximate a selected tissue based on the monitored impedance by comparing the monitored impedance to a threshold value. In some embodiments, the threshold value is acquired by monitoring the impedance of the selected tissue.

In various embodiments, the systems described herein, the electrical monitoring apparatus is further configured to provide an indication to restrict the amount of force applied by the capture device based on the monitored impedance.

In various embodiments, the systems described herein, the electrical monitoring apparatus is further configured to determine whether the capture device has captured the selected tissue based on the monitored impedance.

In various embodiments, the systems described herein may include actuation apparatus operably coupled to the capture device to actuate the capture device to capture the body tissue, wherein the electrical monitoring apparatus is operably coupled to the actuation apparatus and is further configured to actuate the capture device to capture the body tissue using the actuation apparatus based on the monitored impedance.

In various embodiments, the systems described herein, the selected tissue comprises atrial tissue.

In some embodiments, the systems described herein include a capture device configured to capture body tissue; a capture shaft comprising an elongated body comprising a proximal end and a distal end, wherein the distal end of the capture shaft is coupled to the capture device; a capture device electrode coupled to the capture device; a ligation element configured to ligate the body tissue; a ligation element electrode coupled to the ligation element; and electrical monitoring apparatus operably coupled to the capture device and the ligation element electrode. The electrical monitoring apparatus is configured to: monitor an impedance between the capture device electrode and the ligation element electrode; and determine whether the capture device is proximate a selected tissue based on the monitored impedance.

In various embodiments, the systems described herein include a capture device that comprises a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration. In some embodiments, the capture device electrode is coupled to the interior surface of one of the first jaw and the second jaw. In some embodiments, the capture device electrode is coupled to the interior surface of the first jaw and wherein the interior surface of the second jaw is free of any electrodes.

In various embodiments, the systems described herein, the system further comprises force-limiting apparatus operably coupled to the capture device to restrict the amount of force applied by the capture device, wherein the electrical monitoring apparatus is further operably coupled to the force-limiting apparatus and is further configured to use the force-limiting apparatus to restrict the amount of force applied by capture device based on the monitored impedance.

In various embodiments, the systems described herein, the system further comprises force-limiting apparatus operably coupled to the ligation element to restrict the amount of force applied by ligation element when the ligation element is tightened around the body tissue, wherein the electrical monitoring apparatus is further operably coupled to the force-limiting apparatus and is further configured to use the force-limiting apparatus to restrict the amount of force applied by ligation element when the ligation element is tightened around the body tissue based on the monitored impedance.

In various embodiments, the systems described herein, the electrical monitoring apparatus is further configured to provide an indication to a user to restrict the amount of force applied by the capture device based on the monitored impedance.

In various embodiments, the systems described herein, the electrical monitoring apparatus is configured to monitor the impedance between the capture device electrode and the ligation element electrode by monitoring the impedance at a selected frequency between the capture device electrode and the ligation element electrode.

In various embodiments, the systems described herein, the electrical monitoring apparatus is configured to monitor the impedance between the capture device electrode and the ligation element electrode by monitoring the impedance at a selected amplitude between the capture device electrode and the ligation element electrode.

In various embodiments, the systems described herein, the electrical monitoring apparatus is further configured to compare the monitored impedance to a threshold value to determine whether the capture device is proximate the selected tissue. In some embodiments, the threshold value comprises a preselected impedance.

In various embodiments, the systems described herein, the selected tissue comprises atrial tissue.

In various embodiments, the systems described herein include actuation apparatus operably coupled to the capture device to actuate the capture device to capture the body tissue, wherein the electrical monitoring apparatus is operably coupled to the actuation apparatus and is further configured to actuate the capture device to capture the body tissue using the actuation apparatus based on the monitored impedance.

In various embodiments, the systems described herein include actuation apparatus operably coupled to the ligation element to tighten and loosen the ligation element around the body tissue, wherein the electrical monitoring apparatus is operably coupled to the actuation apparatus and is further configured to tighten the ligation element around the body tissue using the actuation apparatus based on the monitored impedance.

In some embodiments, the systems described herein include a capture device configured to capture body tissue; a capture shaft comprising an elongated body comprising a proximal end and a distal end, wherein the distal end of the capture shaft is coupled to the capture device; a ligation element configured to ligate the body tissue; and force-limiting apparatus operably coupled to the ligation element to restrict the amount of force applied by ligation element when the ligation element is tightened around the body tissue. In some embodiments, the force-limiting apparatus comprises a spring operably coupled to the ligation element, a clutch, etc.

In various embodiments, the systems described herein include a force-limiting apparatus operably coupled to the capture device to restrict the amount of force applied by the capture device to the body tissue.

In various embodiments, the systems described herein, the capture device comprises a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration, wherein the force-limiting apparatus is configured to restrict the amount of force applied by the first jaw and the second jaw. In some embodiments, the force-limiting apparatus comprises a spring operably coupled to the first jaw and the second jaw, wherein the spring operates to keep the first jaw and the second jaw in a normally closed configuration. In some embodiments, the force-limiting apparatus comprises a clutch.

In some embodiments, the systems described herein include a capture device configured to capture body tissue; a capture shaft comprising an elongated body comprising a proximal end and a distal end, wherein the distal end of the capture shaft is coupled to the capture device; pressure-sensing apparatus operably coupled to the capture device; and electrical monitoring apparatus operably coupled to the pressure-sensing apparatus. The electrical monitoring apparatus is configured to measure the amount of pressure applied by the capture device.

In various embodiments, the systems described herein, the capture device comprises a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration, wherein the pressure-sensing apparatus is operably coupled to the first jaw and the second jaw of the capture device to monitor the amount of pressure applied by the capture device.

In various embodiments, the systems described herein, the electrical monitoring apparatus is further configured to: compare the monitored pressure applied by the capture device to a threshold value; and determine whether the body tissue is captured by the capture device based on the comparison between the monitored pressure and the threshold value.

In various embodiments, the systems described herein, the electrical monitoring apparatus is further configured to report to a user the amount of pressure applied by the capture device.

In various embodiments, the systems described herein, the electrical monitoring apparatus is further configured to record the pressure applied by the capture device.

In various embodiments, the systems described herein include force-limiting apparatus operably coupled to the electrical monitoring apparatus and to the capture device to restrict the amount of pressure applied by the capture device to the body tissue, wherein the electrical monitoring apparatus is further configured to limit the amount of pressure applied by the capture device based on the comparison between the monitored pressure and the threshold value.

In various embodiments, the systems described herein include actuation apparatus operably coupled to the capture device to actuate the capture device to capture the body tissue, wherein the electrical monitoring apparatus is operably coupled to the actuation apparatus and is further configured to actuate the capture device to capture the body tissue using the actuation apparatus based on the amount of pressure applied by the capture device.

In some embodiments, the systems described herein include a capture device configured to capture body tissue; a capture shaft comprising an elongated body comprising a proximal end and a distal end, wherein the distal end of the capture shaft is coupled to the capture device; temperature-sensing apparatus operably coupled to the capture device; and electrical monitoring apparatus operably coupled to the temperature-sensing apparatus, wherein the electrical monitoring apparatus is configured to monitor the temperature proximate the temperature-sensing apparatus.

In various embodiments, the systems described herein, the capture device comprises a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration.

In various embodiments, the systems described herein, the electrical monitoring apparatus is further configured to: compare the monitored temperature to a threshold value; and determine whether the body tissue is captured by the capture device based on the comparison between the monitored temperature and the threshold value.

In various embodiments, the systems described herein, the electrical monitoring apparatus is further configured to report the monitored temperature to a user to assist in determining whether the body tissue is captured by the capture device.

In various embodiments, the systems described herein include a ligation element configured to ligate the body tissue; and actuation apparatus operably coupled to the ligation element to tighten and loosen the ligation element around the body tissue, wherein the electrical monitoring apparatus is operably coupled to the actuation apparatus and is further configured to tighten the ligation element around the body tissue using the actuation apparatus based on the monitored temperature.

In various embodiments, the systems described herein include actuation apparatus operably coupled to the capture device to actuate the capture device to capture the body tissue, wherein the electrical monitoring apparatus is operably coupled to the actuation apparatus and is further configured to actuate the capture device to capture the body tissue using the actuation apparatus based on the monitored temperature.

In some embodiments, the systems described herein include a capture device configured to capture body tissue; a capture shaft comprising an elongated body comprising a proximal end and a distal end, wherein the distal end of the capture shaft is coupled to the capture device; a ligation element configured to ligate the body tissue; motion-sensing apparatus operably coupled to the capture device; and electrical monitoring apparatus operably coupled to the motion-sensing apparatus. The electrical monitoring apparatus is configured to: monitor the motion of the capture device; and determine whether the ligation element has ligated the body tissue based on the monitored motion of the capture device. In some embodiments, the capture device comprises a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration.

In various embodiments, the systems described herein include actuation apparatus operably coupled to the capture device to actuate the capture device to capture the body tissue, wherein the electrical monitoring apparatus is operably coupled to the actuation apparatus and is further configured to actuate the capture device to capture the body tissue using the actuation apparatus based on the monitored motion of the capture device.

In various embodiments, the systems described herein include actuation apparatus operably coupled to the ligation element to tighten and loosen the ligation element around the body tissue, wherein the electrical monitoring apparatus is operably coupled to the actuation apparatus and is further configured to tighten the ligation element around the body tissue using the actuation apparatus based on the monitored motion of the capture device.

In some embodiments, the systems described herein include a capture device; a capture shaft comprising an elongated body comprising a proximal end and a distal end, wherein the distal end of the capture shaft is coupled to the capture device; pulse oximetry apparatus coupled to the capture device, wherein the pulse oximetry apparatus comprises: a transmitter coupled to the capture device configured to transmit light; and a receiver coupled to the capture device configured to receive light emitted from the transmitter; and electrical monitoring apparatus operably coupled to the pulse oximetry apparatus, wherein the electrical monitoring apparatus is configured to monitor the light received by the receiver. In some embodiments, the capture device comprises a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration. In various embodiments, the transmitter is coupled to the first jaw and the receiver is coupled to the second jaw.

In various embodiments, the systems described herein, the electrical monitoring apparatus is further configured to determine whether the capture device has captured tissue based on the light received by the receiver.

In various embodiments, the systems described herein, the electrical monitoring apparatus is further configured to compare the light received by the receiver to a threshold value to determine whether the capture device has captured the body tissue.

In various embodiments, the systems described herein includes actuation apparatus operably coupled to the capture device to actuate the capture device to capture the body tissue, wherein the electrical monitoring apparatus is operably coupled to the actuation apparatus and is further configured to actuate the capture device to capture the body tissue using the actuation apparatus based on the light received by the receiver.

In various embodiments, the systems described herein include a ligation element configured to ligate the body tissue; and actuation apparatus operably coupled to the ligation element to tighten and loosen the ligation element around the body tissue, wherein the electrical monitoring apparatus is operably coupled to the actuation apparatus and is further configured to tighten the ligation element around the body tissue using the actuation apparatus based on the light received by the receiver.

In some embodiments, the systems described herein include a capture device configured to capture body tissue; a capture shaft comprising an elongated body comprising a proximal end and a distal end, wherein the distal end of the capture shaft is coupled to the capture device; an electrode coupled to the capture device; a ligation element configured to ligate the body tissue; and electrical monitoring apparatus operably coupled to the electrode. The electrical monitoring apparatus is configured to: monitor electrical activity of the body tissue using the electrode; compare the monitored electrical activity to a threshold value; and determine whether the body tissue has been ligated based on the based on the comparison between the monitored electrical activity and the threshold value. In some embodiments, the system may further include a force-limiting apparatus operably coupled to the ligation element to restrict the amount of force applied by ligation element when the ligation element is tightened around the body tissue, wherein the electrical monitoring apparatus is further configured to use the force-limiting apparatus to restrict the amount of force applied by the ligation element based on the comparison between the monitored electrical activity and the threshold value. The force-limiting apparatus may be a spring operably coupled to the ligation element.

In some embodiments, the system may further include actuation apparatus operably coupled to the capture device to actuate the capture device to capture the body tissue, wherein the electrical monitoring apparatus is operably coupled to the actuation apparatus and is further configured to actuate the capture device to capture the body tissue using the actuation apparatus based on the monitored electrical activity.

In various embodiments, the systems described herein include actuation apparatus operably coupled to the ligation element to tighten and loosen the ligation element around the body tissue, wherein the electrical monitoring apparatus is operably coupled to the actuation apparatus and is further configured to tighten the ligation element around the body tissue using the actuation apparatus based on the monitored electrical activity.

In some embodiments, the systems described herein include a ligation element for ligating body tissue, wherein the ligation element comprises a loop; a ligation element lead extending from a first end to a second end and throughout the ligation element; and electrical monitoring apparatus operably coupled to the first end and the second end of ligation element lead. The electrical monitoring apparatus is configured to: monitor an impedance of the ligation element lead; and determine whether the body tissue has been ligated based on the monitored impedance.

In various embodiments, the systems described herein, the electrical monitoring apparatus is further configured to: compare the monitored impedance to a threshold value; and determine whether the body tissue has been ligated based on the comparison between the monitored impedance and a threshold value.

In various embodiments, the systems described herein, the electrical monitoring apparatus is further configured to report the amount of tension within the ligation element based on the monitored impedance.

In various embodiments, the systems described herein include a force-limiting apparatus operably coupled to the ligation element to restrict the amount of force applied by ligation element when the ligation element is tightened around the body tissue, wherein the electrical monitoring apparatus is operably coupled to the force-limiting apparatus and is further configured to use the force-limiting apparatus to restrict the amount of force applied by the ligation element based on the monitored impedance. In some embodiments, the force-limiting apparatus comprises a clutch.

In various embodiments, the systems described herein include actuation apparatus operably coupled to the ligation element to tighten and loosen the ligation element around the body tissue, wherein the electrical monitoring apparatus is operably coupled to the actuation apparatus and is further configured to tighten the ligation element around the body tissue using the actuation apparatus based on the monitored impedance.

Navigation to and capture of the left atrial appendage may be used to provide stability for subsequent procedures. The left atrial appendage may be stabilized and/or captured for any number of procedures including ablation, drug delivery, isolation, ligation, diagnostic mapping, etc. The systems and methods described herein may help navigate to and locate the left atrial appendage through minimally invasive approaches.

Further, the systems and methods described herein may use EGM signals for navigation and tissue capture with respect to the left atrial appendage as well as other navigation techniques, such as, e.g., fluoroscopy, echocardiography, MRI, CT scanning, ultrasonic imaging, direct visualization (using, e.g., fiberoptic devices), etc. Some potentially useful systems and methods for navigation using innate electrical signals such as EGM signals may be described in PCT Application Serial No. US2009/38544, filed Mar. 27, 2009, entitled NAVIGATION AND TISSUE CAPTURE SYSTEMS AND METHODS.

For example, the methods described herein may include navigating a device to an anatomical structure by delivering a device into the anatomical area; injecting image enhancement liquid into the anatomical area; and identifying the location of the device and/or the locations of anatomical structures (e.g., the left atrial appendage) using fluoroscopic or other imaging techniques that may be enhanced by injection of the image enhancement liquid.

In another aspect, a system may be provided that includes a capture device having a first jaw and a second jaw, wherein the first jaw and the second jaw have an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration; a capture shaft having an elongated body with a proximal end and a distal end, wherein the distal end of the capture shaft is attached to the capture device; a capture shaft electrode attached to the capture shaft proximate the distal end of the capture shaft, wherein the capture shaft electrode is located proximal of the capture device; a capture shaft electrode conductor extending from the capture shaft electrode towards the proximal end of the capture shaft, wherein the capture shaft conductor includes an electrical monitoring apparatus connector; a first electrode attached to the capture device; and a first electrode lead extending from the first electrode towards the proximal end of the capture shaft, wherein the first electrode lead has an electrical monitoring apparatus connector.

In another aspect, a method of navigating to selected internal body tissue is described that includes delivering the capture device of a navigation and tissue capture system described herein to an internal body location; monitoring innate electrical activity in tissue proximate the internal body location using the capture shaft electrode; capturing tissue using the capture device; and monitoring innate electrical activity in tissue captured by the capture device. In some embodiments, the internal body location may be the pericardial space and the captured tissue may include the left atrial appendage.

In another aspect, a system is described that includes a delivery device having a proximal end, a distal end, and a capture lumen having an opening proximate the distal end of the delivery device, wherein a longitudinal axis extends between the proximal end and the distal end; a capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a capture shaft having a distal end operably attached to the capture device, the capture shaft extending through the capture lumen from a proximal end of the capture lumen to the capture device; a capture shaft electrode attached to the capture shaft proximate the distal end of the capture shaft, wherein the capture shaft electrode is located proximal of the capture device; a capture shaft electrode conductor extending from the capture shaft electrode towards the proximal end of the capture shaft, wherein the capture shaft conductor includes a connector adapted for connection to an EGM monitoring apparatus; a primary capture electrode attached to the capture device; and a primary capture electrode lead extending from the primary capture electrode towards the proximal end of the delivery device, wherein the primary capture electrode lead includes a connector adapted for connection to an EGM monitoring apparatus.

In another aspect, a system may be provided that includes a delivery device having a proximal end, a distal end, and a capture lumen having an opening proximate the distal end of the delivery device, wherein a longitudinal axis extends between the proximal end and the distal end; a capture device having a first jaw and a second jaw, wherein the first jaw and the second jaw have an open configuration in which the first jaw and the second jaw are open and a closed configuration in which the first jaw and the second jaw are closed; the capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a capture shaft having a distal end operably attached to the capture device, the capture shaft extending through the capture lumen from a proximal end of the capture lumen to the capture device; a capture shaft electrode attached to the capture shaft proximate the distal end of the capture shaft, wherein the capture shaft electrode is located proximal of the capture device; a capture shaft electrode conductor extending from the capture shaft electrode towards the proximal end of the capture shaft, wherein the capture shaft conductor includes an EGM monitoring apparatus connector; a first electrode exposed on an interior surface of the first jaw of the capture device; and a first electrode lead extending from the first electrode towards the proximal end of the delivery device, wherein the first electrode lead includes an EGM monitoring apparatus connector.

In another aspect, a system may be provided that includes a delivery device having a proximal end, a distal end, and a capture lumen with an opening proximate the distal end of the delivery device, wherein a longitudinal axis extends between the proximal end and the distal end; a capture device having a first jaw and a second jaw, wherein the first jaw and the second jaw have an open configuration in which the first jaw and the second jaw are open and a closed configuration in which the first jaw and the second jaw are closed; the capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a capture shaft having a distal end operably attached to the capture device, the capture shaft extending through the capture lumen from a proximal end of the capture lumen to the capture device; a capture shaft electrode attached to the capture shaft proximate the distal end of the capture shaft, wherein the capture shaft electrode is located proximal of the capture device; a capture shaft electrode conductor extending from the capture shaft electrode towards the proximal end of the capture shaft, wherein the capture shaft conductor includes an EGM monitoring apparatus connector; a first electrode and a second electrode, wherein the first electrode and the second electrode are exposed on an interior surface of the first jaw of the capture device; a first electrode lead extending from the first electrode towards the proximal end of the delivery device, wherein the first electrode lead includes an EGM monitoring apparatus connector; and a second electrode lead extending from the second electrode towards the proximal end of the delivery device, wherein the second electrode lead includes an EGM monitoring apparatus connector.

In another aspect, a system may be provided that includes a capture shaft having a proximal end and a distal end, wherein the capture shaft defines a longitudinal axis extending from the proximal end to the distal end; a capture device attached to the distal end of the capture shaft, the capture device having a first jaw and a second jaw, wherein the capture device has a closed configuration in which the first jaw and the second jaw are closed and an open configuration in which the first jaw and the second jaw are open; and wherein at least one of the first jaw and the second jaw rotate about an axis oriented generally transverse to the longitudinal axis of the capture shaft when the first jaw and the second jaw move between the open configuration and the closed configuration; a capture shaft electrode attached to the capture shaft proximate the distal end of the capture shaft, wherein the capture shaft electrode is located proximal of the capture device; a capture shaft electrode conductor extending from the capture shaft electrode towards the proximal end of the capture shaft, wherein the capture shaft conductor includes an EGM monitoring apparatus connector; a first electrode exposed on an interior surface of the first jaw of the capture device; and a first electrode lead extending from the first electrode towards the proximal end of the delivery device, wherein the first electrode lead includes an EGM monitoring apparatus connector.

In another aspect, a system may be provided that includes a capture shaft having a proximal end and a distal end, wherein the capture shaft defines a longitudinal axis extending from the proximal end to the distal end; a capture device attached to the distal end of the capture shaft, the capture device having a first jaw and a second jaw, wherein the capture device has a closed configuration in which the first jaw and the second jaw are closed and an open configuration in which the first jaw and the second jaw are open; and wherein at least one of the first jaw and the second jaw rotate about an axis oriented generally transverse to the longitudinal axis of the capture shaft when the first jaw and the second jaw move between the open configuration and the closed configuration; an external electrode located on an external surface of at least one of the first jaw and the second jaw; and an external electrode lead extending from the external electrode towards the proximal end of the delivery device, wherein the external electrode lead includes an EGM monitoring apparatus connector; a first electrode exposed on an interior surface of the first jaw of the capture device; and a first electrode lead extending from the first electrode towards the proximal end of the delivery device, wherein the first electrode lead includes an EGM monitoring apparatus connector.

In another aspect, a system may be provided that includes a capture shaft having a proximal end and a distal end, wherein the capture shaft defines a longitudinal axis extending from the proximal end to the distal end; a capture device attached to the distal end of the capture shaft, the capture device having a first jaw and a second jaw, wherein the capture device has a closed configuration in which the first jaw and the second jaw are closed and an open configuration in which the first jaw and the second jaw are open, wherein an interior surface of the first jaw is located closer to an interior surface of the second jaw when the first jaw and the second jaw are in the closed configuration than when the first jaw and the second jaw are in the open configuration; an electrode exposed on an interior surface of the first jaw of the capture device; and a first electrode lead extending from the first electrode towards the proximal end of the delivery device, wherein the first electrode lead includes an EGM monitoring apparatus connector; wherein the interior surface of the second jaw does not contain any electrodes capable of sensing innate electrical activity of tissue located between the first jaw and the second jaw.

In another aspect, a system may be provided that includes a capture shaft having a proximal end and a distal end, wherein the capture shaft defines a longitudinal axis extending from the proximal end to the distal end; a capture device attached to the distal end of the capture shaft, the capture device having a first jaw and a second jaw, wherein the capture device has a closed configuration in which the first jaw and the second jaw are closed and an open configuration in which the first jaw and the second jaw are open, wherein an interior surface of the first jaw is located closer to an interior surface of the second jaw when the first jaw and the second jaw are in the closed configuration than when the first jaw and the second jaw are in the open configuration; a first electrode exposed on an interior surface of the first jaw of the capture device, wherein the first electrode occupies about one quarter or more of the interior surface of the first jaw; and a first electrode lead extending from the first electrode towards the proximal end of the delivery device, wherein the first electrode lead includes an EOM monitoring apparatus connector.

In another aspect, a system may be provided that includes a delivery device having a proximal end, a distal end, and a capture lumen having an opening proximate the distal end of the delivery device, wherein a longitudinal axis extends between the proximal end and the distal end; a delivery device electrode attached to the delivery device proximate the distal end of the delivery device; a delivery device electrode lead extending from the delivery device electrode towards the proximal end of the delivery device, wherein the delivery device electrode lead includes a connector adapted for connection to an EGM monitoring apparatus; a capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a primary capture electrode attached to the capture device; and a primary capture electrode lead extending from the primary capture electrode towards the proximal end of the delivery device, wherein the primary capture electrode lead includes a connector adapted for connection to an EGM monitoring apparatus.

In another aspect, a capture system may be provided that includes a delivery device comprising a proximal end, a distal end, and a capture lumen comprising an opening proximate the distal end of the delivery device, wherein a longitudinal axis extends between the proximal end and the distal end; a capture device sized for movement within the capture lumen of the delivery device, wherein the capture device includes a delivery configuration in which a distal end of the capture device is contained within the capture lumen, and wherein the capture device has an extended configuration in which the distal end of the capture device extends out of the capture lumen proximate the distal end of the delivery device; a primary capture electrode attached to the capture device; and a primary capture electrode lead extending from the primary capture electrode towards the proximal end of the delivery device, wherein the primary capture electrode lead includes a connector adapted for connection to an EGM monitoring apparatus.

Any of the systems described herein may include an EGM monitor device capable of displaying EGM signals obtained from one or more electrodes provided in the systems.

Any of the systems described herein may include a delivery device and/or a capture shaft that includes at least one image enhancement liquid injection lumen having an injection opening proximate the distal end of the delivery device and/or the capture shaft.

In another aspect, a kit may be provided that includes any of the navigation and tissue capture systems described herein along with an image enhancement liquid injection device. The kit may further include a container of image enhancement liquid.

In another aspect, a method of navigating a device to the left atrial appendage may be provided that includes delivering a device into the pericardial sac; detecting an EGM signal within the pericardial sac using one or more electrodes on the device; identifying the location of the device relative to the left atrial appendage by determining if the EGM signal is associated with atrial epicardial tissue; optionally confirming capture of the left atrial appendage by a capture device by determining if an EGM signal obtained from tissue captured by the capture device is associated with tissue of the left atrial appendage; and optionally confirming capture of atrial tissue by electrically stimulating the atrial tissue and confirming that the tissue is being paced.

In another aspect, a system is provided that includes a delivery device having a proximal end, a distal end, and a capture lumen that includes an opening proximate the distal end of the delivery device, wherein a longitudinal axis extends between the proximal end and the distal end; a delivery device electrode attached to the delivery device proximate the distal end of the delivery device; a delivery device electrode lead extending from the delivery device electrode towards the proximal end of the delivery device, wherein the delivery device electrode lead comprises a connector adapted for connection to an EGM monitoring apparatus; a capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a primary capture electrode attached to the capture device; and a primary capture electrode lead extending from the primary capture electrode towards the proximal end of the delivery device, wherein the primary capture electrode lead includes a connector adapted for connection to an EGM monitoring apparatus.

In various aspects, the systems may include one or more of the following features. The primary capture electrode may be located within the capture lumen when the capture device is in the delivery configuration, and the primary capture electrode may be located outside of the capture lumen when the capture device is in the extended configuration. The capture device may be a grasping apparatus that includes a first jaw and a second jaw, wherein closure of the grasping apparatus includes movement of the first jaw and the second jaw towards each other to capture tissue between the first jaw and the second jaw; the primary capture electrode may be attached to the first jaw; the capture device may include an auxiliary capture electrode attached to the second jaw. The primary capture electrode and the auxiliary capture electrode may be arranged such that closure of the grasping apparatus in the absence of tissue between the first jaw and the second jaw causes the primary electrode and the auxiliary electrode to contact each other. The first jaw and the second jaw may be arranged opposite from each other, and wherein the first jaw and the second jaw both include an internal surface facing the opposing jaw and an external surface facing away from the opposing jaw, and further wherein the primary capture electrode is located on one of the external surfaces of the first jaw and the second jaw. A first jaw electrode may be located on the internal surface of the first jaw and a second jaw electrode may be located on the internal surface of the second jaw, wherein the first jaw electrode and the second jaw electrode may be arranged such that closure of the grasping apparatus in the absence of tissue between the first jaw and the second jaw causes the first jaw electrode and the second jaw electrode to contact each other. The system may include a return and/or tracking electrode adapted for attachment to the skin of a patient. The capture device may include a barbed hook, a tissue screw; a cryogenic device; a cage, a lasso, a suction device, adhesive, RF energy, etc. The delivery device may include a ligation lumen having a ligation opening proximate the distal end of the delivery device. The system may include an EGM monitor device capable of displaying EGM signals obtained from one or more electrodes of the tissue capture system.

In another aspect, a system may be provided that includes a delivery device having a proximal end, a distal end, and a capture lumen that includes an opening proximate the distal end of the delivery device, wherein a longitudinal axis extends between the proximal end and the distal end; a capture device sized for movement within the capture lumen of the delivery device, wherein the capture device has a delivery configuration in which a distal end of the capture device is contained within the capture lumen, and wherein the capture device has an extended configuration in which the distal end of the capture device extends out of the capture lumen proximate the distal end of the delivery device; a primary capture electrode attached to the capture device; and a primary capture electrode lead extending from the primary capture electrode towards the proximal end of the delivery device, wherein the primary capture electrode lead includes a connector adapted for connection to an EGM monitoring apparatus.

In another aspect, a method is provided that may include navigating a device to the left atrial appendage by delivering a device into the pericardial sac; detecting an EGM signal within the pericardial sac using one or more electrodes on the device; identifying the location of the device relative to the left atrial appendage by determining if the EGM signal is associated with atrial epicardial tissue; optionally confirming capture of the left atrial appendage by a capture device by determining if an EGM signal obtained from tissue captured by the capture device is associated with tissue of the left atrial appendage.

Further, the navigation and capture systems described herein may be integrated with various other systems including, e.g., NavX/Carto systems, TEE Doppler flow imaging systems, etc.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an electrode may be used to refer to one, two, three or more electrodes.

The term "and/or" means one or all of the listed elements or a combination of any two or more of the listed elements.

The above summary is not intended to describe each embodiment or every implementation of the systems and methods described herein. Rather, a more complete understanding of the systems and methods described herein will become apparent and appreciated by reference to the following Detailed Description of Exemplary Embodiments and claims in view of the accompanying figures of the drawing.

BRIEF DESCRIPTION OF THE VIEWS OF THE DRAWING

FIG. 7 is a cross-sectional view of the human heart showing the left side anatomy, with the capture device of FIG. 1 capturing the left atrial appendage.

FIG. 8A depicts a representative electrogram (EGM) across the interior electrodes on the jaws of the capture device of FIG. 7.

FIG. 8B depicts a representative electrogram (EGM) as detected by the external electrode while grasping the left atrial appendage tissue.

FIG. 9 is a cross-sectional view of the human heart depicting closure of the capture device of FIG. 1 in a situation where the capture device does not capture left atrial appendage tissue.

FIG. 10A depicts a representative electrogram (EGM) across the interior electrodes on the jaws of the capture device of FIG. 9 when the jaws do not capture tissue.

FIG. 10B depicts a representative electrogram (EGM) as detected using the exterior electrode when the jaws do capture left atrial appendage tissue.

FIG. 11 is a cross-sectional view of the human heart depicting advancement of a capture device past the distal tip of the left atrial appendage lobe.

FIG. 12 is a cross-sectional view of the human heart depicting the capture device after advancement beneath the distal tip of the left atrial appendage lobe.

FIG. 13A depicts a representative electrogram (EGM) across the interior electrodes on the jaws of the capture device of FIG. 12.

FIG. 13B depicts a representative electrogram (EGM) as detected by the exterior electrode on the capture device of FIG. 12.

FIGS. 26 & 27 depict two different embodiments of ligation elements including electrodes.

DESCRIPTION OF EXEMPLARY EMBODIMENTS

Figure 1:
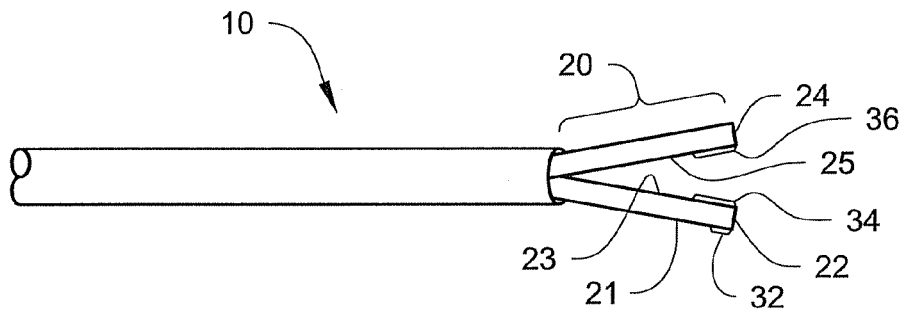
FIG. 1 depicts one exemplary embodiment of a delivery device with a capture device extending out of a delivery lumen in the delivery device.

In the following description of exemplary embodiments, reference is made to the accompanying figures of the drawing which form a part hereof, and in which are shown, by way of illustration, specific embodiments in which the systems and/or methods may be practiced. It is to be understood that other embodiments may be utilized and structural changes may be made without departing from the scope of the present invention.

One exemplary embodiment of a tissue capture system including a delivery device 10 and a capture device 20 is depicted in FIG. 1. The delivery device 10 may be provided in the form of, e.g., a sheath (that may or may not be provided with an introducer/dilator as is known), catheter, or other elongate structure. The delivery device 10 may or may not be flexible. The delivery device 10 itself may preferably be steerable or deflectable. The delivery device 10 is also optional, i.e., the navigation and tissue capture systems described herein may not include a delivery sheath.

The proximal end of the capture device 20 may preferably include a user interface that allows an operator to deploy and retract the capture device 20 from within the delivery device 10, a mechanism to actuate the capture device 20, and optionally a mechanism to steer the capture device separately from the delivery device 10.

In the depicted embodiment, the delivery device 10 includes a lumen through which the capture device 20 can be advanced or retracted to assist with delivery of the capture device 20 to a selected internal body location. Although the delivery device 10 may include as few as one lumen as depicted in FIG. 1, it may include two or more lumens that may be used to provide pathways to deliver other devices, provide visual access, fluid access, etc. The capture device 20 may preferably extend out of the proximal end of the delivery device 10 such that it can be controlled by a user also operating the delivery device 10 as is conventional in the use of minimally invasive surgical devices.

The capture device 20 is depicted in FIG. 1 in an extended configuration in which the distal end of the capture device 20 extends out of the lumen in the delivery device 10 proximate the distal end of the delivery device 10. Although not depicted, the capture device 20 is preferably movable within the lumen of the delivery device 10 such that the capture device 20 can be moved between the extended position depicted in FIG. 1 and a delivery configuration in which a distal end of the capture device 20 is contained within the lumen of the delivery device 10. A potential benefit of having the capture device 20 retracted into the delivery device 10 during delivery is a reduction in the likelihood of trauma to the epicardial surface at the delivery site and on the path to the delivery site (e.g., a left atrial appendage).

The capture device 20 depicted in FIG. 1 is in the form of a grasping apparatus that includes two jaws 22 and 24. The jaws 22 and 24 can preferably be moved between on open position adapted to allow tissue to enter the space between the open jaws 22 and 24 and a closed position in the jaws 22 and 24 are moved towards each other to capture tissue that can be grasped between the jaws 22 and 24. The jaws of the grasping apparatus can be actuated by any suitable technique (e.g., mechanical linkage, memory material that is closed when drawn into the delivery device, electrical activation, hydraulically, pneumatically, magnetically, etc.). Although the grasping apparatus of the capture device 20 includes two jaws, it should be understood that other grasping apparatus may be provided that include three or more jaws (and that other apparatus for capturing tissue may be used in place of, or in addition to, apparatus that use jaws).

Also, although the exemplary systems and methods are described in connection with a grasping apparatus as a tissue capture device, it should be understood that the systems and methods may be used in connection with a wide variety of capture devices. Potentially useful alternative capture devices may include, but are not limited to, helix groups, cryogenic tips, barbed hooks, cages, adhesive structures, suction, laser energy, RF energy, etc. Examples of some potentially suitable capture devices and/or systems may be described in U.S. Pat. Nos. 7,338,434; 7,141,057; 7,276,235; 6,206,827; etc.

The capture device 20 depicted in FIG. 1 includes electrodes that can be used to detect EGM signals for navigating the delivery device 10 and the capture device 20. The particular arrangement of electrodes depicted in connection with the system of FIG. 1 includes electrodes 32, 34, and 36. The electrode 32 may be located on an external surface 21 of the jaw 22 (where the external surface 21 is the surface of the jaw 22 that faces away from the opposing jaw 24). The electrode 34 may be located on an internal surface 23 of the jaw 22 (where the internal surface 23 is the surface of the jaw 22 that faces the opposing jaw 24). The electrode 36 may be located on an internal surface 25 of the jaw 24 (where the internal surface 25 is the surface of the jaw 24 that faces the opposing jaw 22). The electrodes may be placed in any suitable location along the length of the jaws, e.g., the distal end, proximal end or any intermediate location.

The proximal end of the capture device 20 preferably includes connectors connected to each electrode on the distal end of the capture device 20 by leads such that the electrodes can be connected to a system capable of generating user-readable plots of the electrical energy detected using the electrodes. Such systems will be well-known to those of skilled in the art. For example, when inside the pericardial space, the electrodes at the working or distal end of the capture device 20 can be used to detect the electrogram (EGM) on the epicardial surface of the patient's heart. Any or all of the electrodes may be monopolar or multipolar, as desired.

Figure 2A:
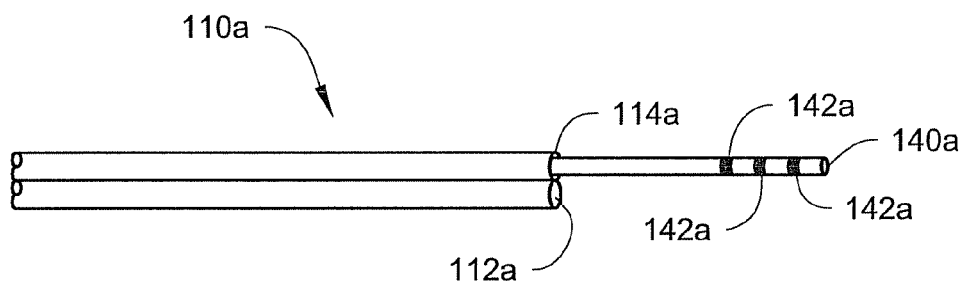
FIG. 2A depicts another exemplary embodiment of a delivery device including a mapping device extending therefrom.

FIG. 2A depicts another system that may be used to navigate to and capture selected tissue. In this depicted embodiment, the delivery device 110a includes two lumens 112a and 114a, with the lumen 112a preferably being used to delivery a capture device (not shown). The lumen 114a is used to deliver a mapping device 140a that, in the depicted embodiment, can be extended out of the lumen 114a.

The mapping device 140a may be in the form of, e.g., a conventional electrophysiology mapping catheter. The mapping device 140a may include as few as one electrode 142a or two or more electrodes 142a. The electrode or electrodes 142a may be monopolar or multipolar.

Although the delivery device 110a could be used with a capture device deployed down the lumen 112a as described above, the delivery device could potentially include a capture device delivered through the same lumen as the mapping device 140a (with the mapping device being deployed, e.g., through a channel provided in the capture device itself). Secondly the device in FIG. 2 may be used independently to find the left atrial appendage based on the electrocardiogram (EGM) and then held in place while a second stabilization/capture device (mechanical grasper, helix group, cryo tip, barbed hook) was deployed to the same location (e.g., over the mapping device 140a or over the delivery device 110a) to grab/stabilize the required tissue.

Figure 2B:
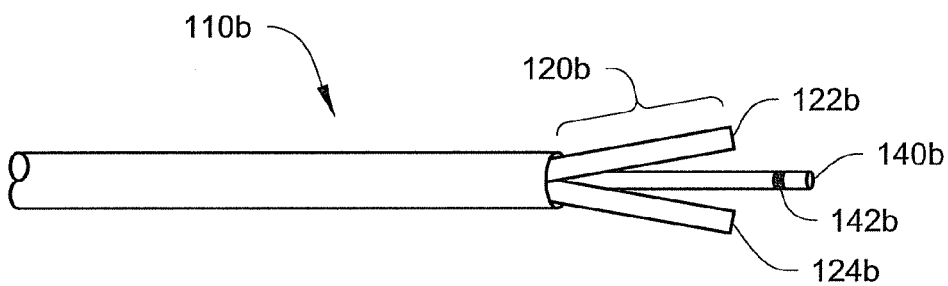
FIG. 2B depicts another exemplary embodiment of a delivery device with a capture device extending out of a delivery lumen in the delivery device and a mapping device extending out of the capture device.

An embodiment in which a mapping device 140b is delivered through a lumen provided in the capture device 120 itself is depicted in FIG. 2B. The mapping device 140b may preferably include an electrode 142b at its distal-most end and/or merely proximate its distal-most end. The capture device 120b may include jaws 122b and 124b that may be used to grasp tissue as described herein. The jaws 122b and 124b and/or the delivery device 110b may or may not include electrodes to assist with navigation.

In the embodiment depicted in FIG. 2B, the capture device 120b may include, for example, a capture shaft (see, e.g., FIGS. 18-20) that includes a lumen through which the mapping device 140b can be advanced and/or retracted. In use, the mapping device 140b may be advanced ahead of the capture device 120b to detect electrical signals in tissue that would then be contacted by the capture device 120b if it were advanced over the mapping device 140b.

Although the depicted embodiment includes a capture device 120b with open jaws, in some embodiments, the capture device may be retained in a closed position while the mapping device is advanced through the closed capture device. In still another variation, the capture device 120b may even be retained within the delivery device 110b while the mapping device 140b is advanced out of the delivery device 110b.

Figure 3:
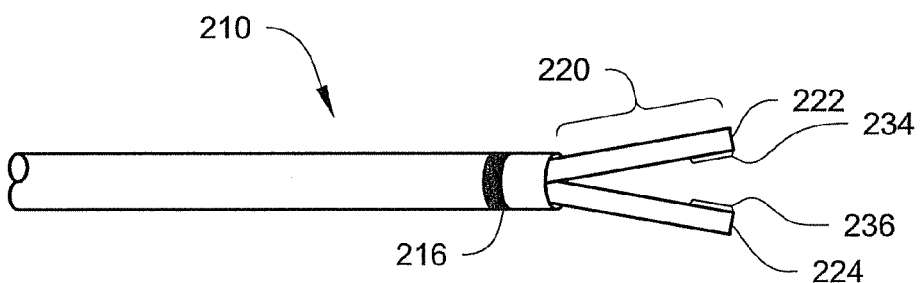
FIG. 3 depicts another exemplary embodiment of a delivery device with a capture device extending out of a delivery lumen in the delivery device.

FIG. 3 depicts another exemplary embodiment of a navigation and tissue capture system that includes a delivery device 210 and a capture device 220. In most respects, the delivery device 210 and the capture device 220 are similar to those depicted and described in connection with FIG. 1. Among the differences are that the delivery device 210 itself includes an electrode 216 located near or proximate its distal end. Although only one electrode 216 is depicted, the delivery device 210 may include two or more electrodes. Also, any electrodes included with the delivery device 210 may be monopolar or multipolar. The electrode 216 may be in the form of a ring electrode as depicted. Alternatively, the electrode or electrodes provided on the delivery device 210 may not be in the form of ring electrodes.

The capture device 220 depicted in FIG. 3 also includes electrodes 234 and 236 on the internal surfaces of the jaws 222 and 224. Although not depicted, the capture device 220 may include other electrodes on, e.g., one or more of the external surfaces of the jaws 222 and 224. The electrode 216 on the delivery device 210 may potentially be used in conjunction with electrodes 234 and 236 on the jaws 222 and 224 to improve navigation and/or to establish the position of the distal end of the capture device 220. The electrode 216 on the delivery device 210 could be used by the operator to help differentiate between tissue (e.g., ventricular and atrial tissue) before the capture device 220 is extended out of the delivery device 210.

One potential advantage of the system depicted in FIG. 3 may be that the distal end of the delivery device 210 could be less traumatic (e.g., softer, smoother, etc.) to the surrounding tissue (e.g., the epicardial surface of the heart) than the capture device 220. After the distal end of the delivery device 210 is in or near a selected internal body location (e.g., the pericardial space) the delivery device 210 (which may preferably be steerable/deflectable) could be navigated to a selected location using the electrode 216 on the delivery device 210 (while the capture device 220 and its electrodes remain in the delivery device 210).

After the distal end of the delivery device is in or near the selected tissue to captured, the capture device 220 may be deployed from the delivery device 210. The electrode or electrodes on the capture device may then be used (alone or in conjunction with the electrode 216 on the delivery device 210) to navigate the capture device 220 to the selected tissue. The electrodes on the capture device 220 may, for example, be able to more accurately assess tissue differentiation. The electrode 216 on the delivery device may, for example, be monitored to determine if the delivery device 210 moves during deployment and use of the capture device 220 (for example, a change in EGM signal seen using the electrode 216 during the grasping of the left atrial appendage may indicate that the delivery device 210 has moved to a less desirable location).

Figure 4:
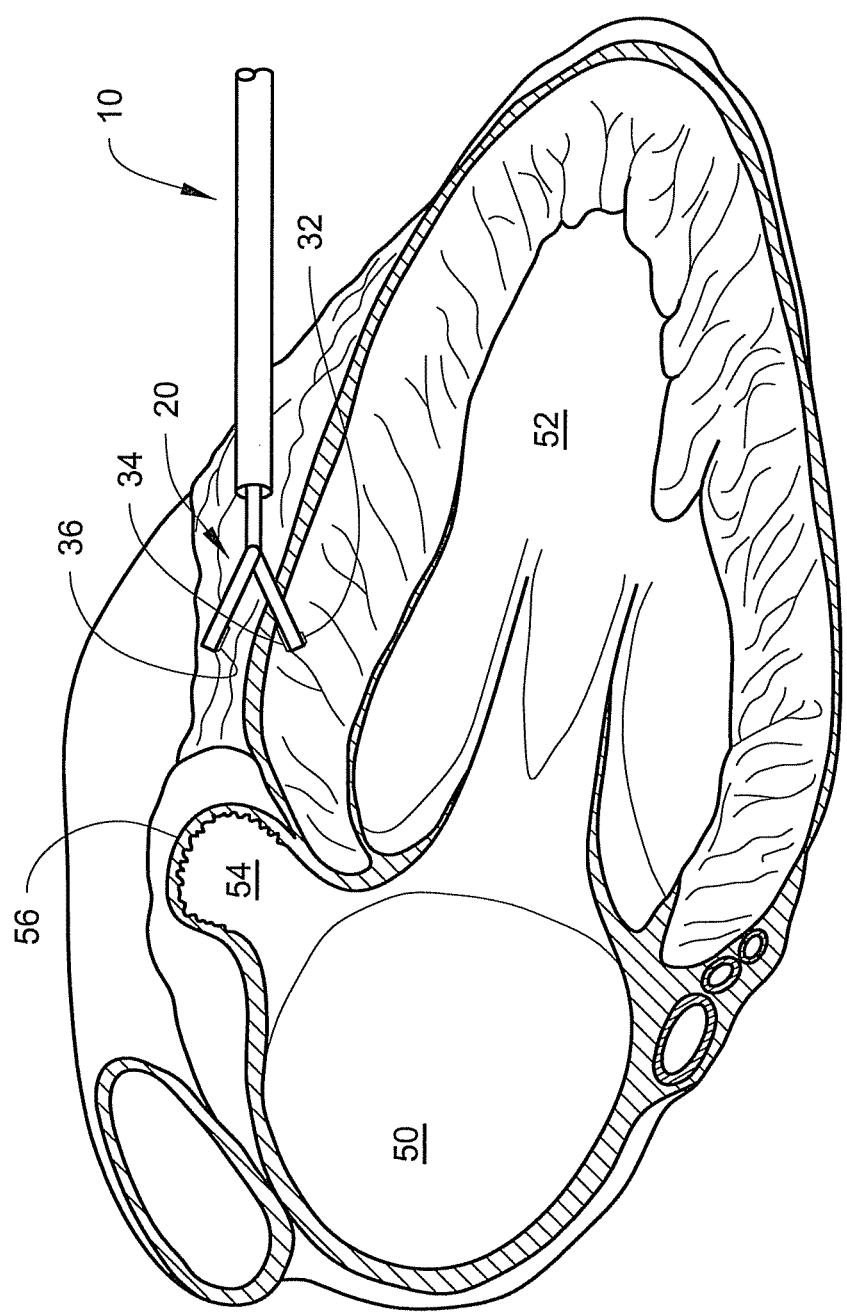
FIG. 4 is a cross-sectional view of a human heart showing the left side anatomy, with the delivery device and capture device of FIG. 1 on the epicardial surface of the human heart.

A cross-sectional view of the left side of the human heart is depicted in FIG. 4 and will be used to describe operation of one embodiment of a navigation and tissue capture system. The heart as depicted includes the left atrium 50 and left ventricle 52. The left atrial appendage 54 extends from the left atrium 50 and includes a distal tip or leading edge 56.

Also depicted in FIG. 4 is the navigation and capture system of, e.g., FIG. 1 including a delivery device 10 and a capture device 20. The capture device 20 includes an external electrode 32 on an external surface of one jaw of the capture device 20 and a pair of internal electrodes 34 and 36 on the internal surfaces of the jaws. The delivery device 10 is depicted as approaching the left atrial appendage 54 from the apex of the heart (which would be typical for a sub-xiphoid approach).

The distal end of the capture device 20 is advanced along the epicardial surface (e.g., over the left ventricle 52) towards the leading edge 56 of the left atrial appendage 54. As can be seen in FIG. 4, a capture device 20 that progresses along the epicardial surface coming from the apex of the heart is primarily in contact with ventricular myocardium tissue 52 until it reaches the leading edge 56 of the left atrial appendage 54. Although not depicted in FIG. 4, there is a thin pericardial membrane that covers the entire epicardial surface of the heart. This pericardial membrane is electrically inactive and does not produce an independent EGM signal.

Ventricular epicardial myocardium tissue 52 produces a distinct EGM compared with the EGM produced by atrial epicardial myocardium tissue such as that found in the leading edge 56 of the left atrial appendage 54. As the capture device 20 advances across the ventricular epicardial myocardium tissue 52 on the epicardial surface of the heart, the electrodes 32 and 36 will primarily capture only ventricular EGM signals. Although not depicted, the delivery device 10 may, itself, also include one or more electrodes (as, for example, described in the system of FIG. 3). Such electrodes may be used in addition to or in place of the electrodes on the capture device 20 (which may or may not be extended out of the delivery device 10).

Depending on the orientation, number, and/or positions of the various electrodes, it may be possible to detect non-ventricular signals on some of the electrodes. For example, electrode 36 may not be in contact with any ventricular tissue and, thus, may detect a minimal EGM signal, while the electrode 32 may be in direct contact with the ventricular myocardium 52 and would likely show a strong near-field ventricular EGM signal.

The device can optionally be designed to maintain orientation such that any one electrode could be maintained in one stationary location relative to a selected part of the anatomy. With respect to FIG. 4, for example, it may be desirable to keep electrode 32 on the epicardial surface versus on the pericardium. That positioning could potentially be maintained by monitoring the electrode 32 and manipulating the devices such that a strong near-field ventricular EGM signal is continually detected by the electrode 32. In another alternative, if no external electrode 32 is provided on the capture device 20, an operator could, for example, monitor the electrodes 34 and 36 on both jaws of the capture device 20 to determine whether the EGM signal detected from one electrode indicates that its jaw is located closer to the ventricular tissue than the other jaw (or that both jaws show an equal signal strength indicating that both jaws are equally close to the ventricular tissue).

Figure 5:
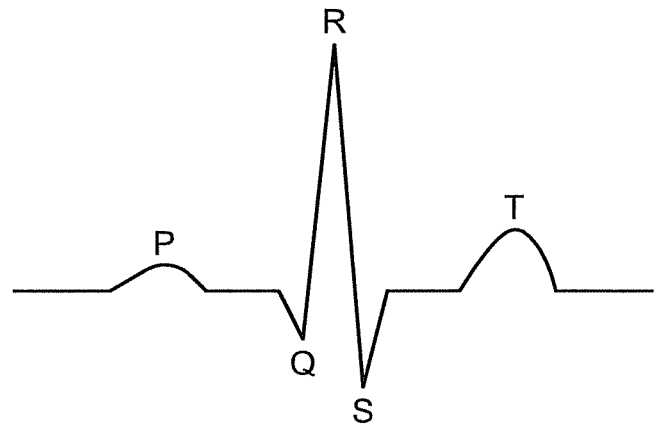
FIG. 5 depicts an exemplary EGM signal from of a normal heartbeat (or cardiac cycle) including a P wave, a QRS complex and a T wave. The EGM signal corresponds to the depolarization of the atria and ventricles.
Figure 6A:
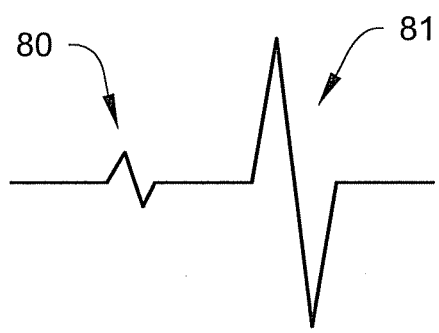
FIGS. 6A-6C depict exemplary electrocardiogram (EGM) signals seen as a device is advanced from the apex of the human heart towards the left atrial appendage.
Figure 6B:
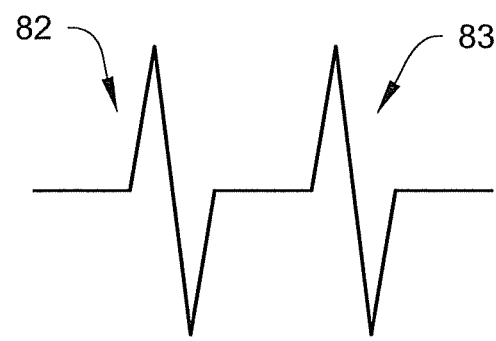
Figure 6C:
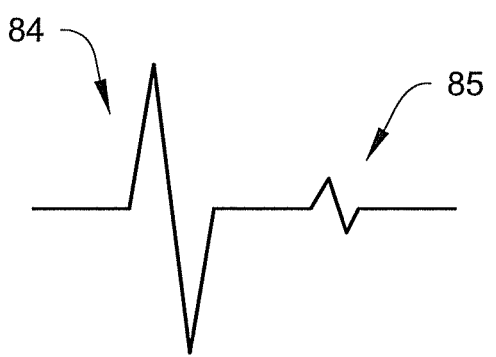

The typical EGM signal associated with a normal human heartbeat (or cardiac cycle) includes a P wave, a QRS complex and a T wave as depicted in FIG. 5. FIGS. 6A-6C depict the EGM signals that may be detected in various locations over the heart. The differences in the EGM signals can be used to determine the position of the electrodes (and thus the devices carrying them) relative to the anatomy of the heart. In some instances, it may be helpful to obtain an electrocardiogram (ECG) signal (using, e.g., surface electrodes as is known conventionally) in addition to the intracardiac EGM signals. The ECG signal may then potentially be used to assist in the navigation process (by, e.g., signal subtraction, etc.).

FIG. 6A represents a potential EGM signal at the initial access point of the sub-xiphoid approach near the apex of the heart. At the apex of the heart there will be a small or insignificant atrial EGM signal (P wave) 80 and a much more pronounced higher amplitude and strong ventricular signal (QRS complex) 81. When the recording electrode is at the apex of the heart or near primarily ventricular tissue the P wave (atrial electrical signal) 80 is much weaker and the QRS complex (ventricular electrical signal) 81 is much stronger with higher amplitude on the EGM tracing.

FIG. 6B depicts a typical EGM tracing as an electrode approaches both atrial and ventricular epicardial tissue. The P wave 82 in FIG. 6B has a much larger amplitude as the electrodes come in contact with atrial tissue (i.e., larger than when the electrodes are at the apex of the heart as seen in FIG. 6A). The QRS complex 83 of FIG. 6B continues to have a large amplitude due to continued contact with ventricular tissue.

FIG. 6C depicts the typical EGM tracing potentially seen using electrodes that are in contact with only atrial tissue such as, e.g., the tissue of the left atrial appendage (which produces strong atrial EGM signals). The EGM signal of FIG. 6C shows a large amplitude P wave 84 and a relatively small amplitude QRS complex signal 85. If the capture device is in the form of a grasping apparatus including jaws, the electrodes that could produce the signal seen in FIG. 6C may be on opposing sides of the left atrial appendage, with the left atrial appendage tissue captured between the jaws. In such an arrangement, capture of electrically active tissue (such as the left atrial appendage) can be distinguished from the capture of electrically inactive tissue (such as, e.g., the pericardium, epicardial fat pads, etc.) using the electrodes on the interior surfaces of the jaws.

Distinguishing between the different EGM signals may preferably be performed by the operator (e.g., the physician), although, in some systems and methods, the distinguishing may be performed with the assistance of an automated system that compares the detected EGM signals with those associated with one or more desired outcomes.

FIG. 7 is another cross-sectional view of a human heart depicting the left-side anatomy in which the navigation/capture system depicted in FIG. 4 is advanced further towards the left atrial appendage 54. Recording electrodes 34 and 36 on the capture device 20 are in direct contact with the epicardial surface of the left atrial appendage 54. The electrode 32 on the external surface of the capture device 20 is still in contact with ventricular tissue.

As a result, the EGM signals detected from the external electrode 32 would differ from the EGM signals detected using the internal electrodes 34 and 36. The different EGM signals would provide a user with the ability to determine that the capture device 20 had, in fact, captured left atrial appendage tissue. Left atrial appendage tissue is the first tissue that produces an atrial EGM when approaching the left atrium from the apex of the heart through a sub-xiphoid access point.

The EGM signal detected between electrodes 34 and 36 would show a strong near-field P wave with high amplitude (atrial electrical activity) and a small amplitude QRS complex (ventricular electrical activity) as depicted in FIG. 8A. In contrast, the external electrode 32 would show a large amplitude QRS complex and potentially and either small or large amplitude P wave depending on its contact with left atrial appendage tissue as depicted in FIG. 8B. It should be noted that the space between the epicardial surface of the heart in the pericardial sac is often full of fluid which may be electrically conductive and may distort the EGM signal slightly when not in direct contact with myocardial tissue.

FIG. 7 provides an opportunity to visualize how the systems and methods described herein may allow the operator to navigate from the apex of the heart (where initial contact is with the epicardial surface during a sub-xiphoid approach) to the tip of the left atrial appendage. As the delivery device 10 (and associated capture device 20) advance across the surface of the heart, the initial EGM signals will indicate contact with ventricular tissue (see, e.g., FIG. 6A). The first EGM signal indicating contact with atrial tissue when approached from the apex of the heart (using, e.g., sub-xiphoid access) should be the tissue of the left atrial appendage.

Further guidance to supplement the use of EGM signals during the procedure may be obtained using other imaging/guidance modalities such as, e.g. fluoroscopy, direct visualization, ultrasound imaging, MRI imaging, CT scans, etc. The use of a secondary imaging/guidance technique may be used to potentially confirm capture of the left atrial appendage by, e.g., providing information regarding the angle of closure of the jaws of a grasping apparatus, etc. If, for example, no tissue is captured, then the jaws of a grasping apparatus may close completely. When tissue is present, the jaws will typically not close completely.

FIG. 9 depicts a situation in which the capture device 20 (and associated delivery device 10) of FIG. 4 is advanced towards the left atrial appendage, but is closed without capturing the tissue of the left atrial appendage. One potential benefit of using EGM signals to navigate to and/or confirm capture of the left atrial appendage tissue is that when the electrodes on a capture device 20 close without capturing tissue between them, the EGM signal would not show a strong amplitude P wave. Rather, the electrodes 34 and 36 would be expected to short out and show a flat line EGM signal as depicted in FIG. 10A because the electrical potential across the electrodes 34 and 36 is zero. If the operator only grabs a small portion of the left atrial appendage tissue in the capture device 20, there also may not be enough impedance, with the result being, again, a flat line EGM signal as depicted in FIG. 10A. In this case, an operator could re-open the capture device 20 and reposition it until the electrodes 34 and 36 indicate a strong amplitude P wave and corresponding contact with left atrial appendage tissue.

In the situation depicted in FIG. 9, the external electrode 32 on the capture device 20 would typically be expected to show a large amplitude QRS complex and potentially and either small or large amplitude P wave depending on its contact with left atrial appendage tissue as depicted in FIG. 10B.

FIG. 11 depicts another situation in which the capture device 20 (and associated delivery device 10) are advanced too far. When the capture device 20 is advanced past the tip of the left atrial appendage that is closest the apex of the heart, it will likely not come into contact with any other atrial tissue. Any tissue that is captured by the capture device 20 as depicted in FIG. 11 will have an non-atrial EGM signal. The electrodes 34 and 36 on the capture device 20 may, for example, reflect an EGM signal of the pericardium or far-field ventricular and/or atrial signals. The external electrode 32 on the capture device 20 may reflect a strong atrial EGM signal given that it may still be in contact with the left atrial appendage as the capture device 20 passes over the appendage (which may be an indication that the capture device 20 is incorrectly positioned). When the LAA is properly positioned in the capture device 20, the external electrode 32 should detect at least some ventricular EGM signal as discussed herein.

FIG. 12 depicts another situation in which the capture device 20 (and associated delivery device 10) are advanced into a position that is not amenable to proper capture of the left atrial appendage. In this situation, the capture device 20 is depicted as advanced beneath the tip of the left atrial appendage, such that the capture device 20 is located between the left atrial appendage and the underlying ventricular tissue. In such an arrangement, it would be unlikely that the capture device 20 could properly capture left atrial appendage tissue for a subsequent procedure. Tissue that is captured when the capture device 20 is beyond the position depicted in FIG. 12 could likely be ventricular tissue with a ventricular EGM signal across electrodes 34 and 36 on the capture device 20.

Confirmation of the situation depicted in FIG. 12 could potentially be obtained if the EGM signals from the electrodes 34 and 36 on the capture device showed both atrial and ventricular signatures as depicted in, e.g., FIG. 13A. In addition, the external electrode 32 may, if it located nearest the ventricular tissue, show an EGM signal weighted towards the QRS complex portion of the complete EGM signal as depicted in FIG. 13B.

The situation depicted in FIG. 12 may not, however, be entirely hopeless. The capture device 20 could potentially capture a lobe of the left atrial appendage and this could be a clinically acceptable outcome. Confirmation of this outcome could potentially be obtained by, e.g., detecting a strong atrial EGM signal (see, e.g., FIG. 6C) using the electrodes 34 and 36 on the capture device 20.

Figure 14:
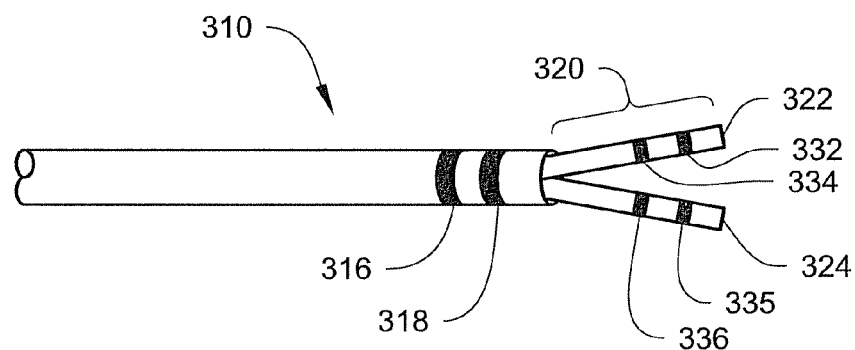
FIG. 14 depicts another exemplary embodiment of a delivery device with a capture device extending out of a delivery lumen in the delivery device.

FIG. 14 depicts another exemplary embodiment of a delivery device 310 and a capture device 320 similar to those depicted in FIGS. 1 and 3. Unlike the devices in those figures, the electrodes 316 and 318 on the delivery device 310 and the electrodes 332, 333, 334, and 335 on the capture device 320 are all ring electrodes. The ring electrodes 316 and 318 on the delivery device 310 could, however, be used in conjunction with electrodes on the jaws 322 and 324 to improve navigation to the left atrial appendage by potentially more precisely establishing position of the distal ends of the jaws 322 and 324 of the capture device 320. Any or all of the electrodes could be monopolar or multipolar.

The electrodes 316 and 318 on the delivery device 310 could be used by the operator to help differentiate between the ventricular and atrial tissue as the delivery device 310 is advanced. Additional specificity of EGM interpretation is potentially feasible with the electrode configuration depicted in FIG. 14. For example, reading a bi-polar signal across electrode 332 and 334 on jaw 322 or electrode 335 and 336 on jaw 324 may allow the operator to better confirm the presence of particular types of tissue within the capture device 320 (i.e., ventricular tissue versus atrial tissue).

The electrodes on the jaws 322 and 324 of the device depicted in FIG. 14 may also create a near-field EGM. The near-field EGM signal may produce a cleaner and easier to interpret EGM signal for determination of tissue type. The ring electrodes 316 and 318 on the delivery device 310 could be used for navigation in the pericardial space in a similar manner as described above for the device depicted in FIG. 3, yet with the potential for a more precise near-field EGM created from the two ring electrodes 316 and 318.

Figure 15:
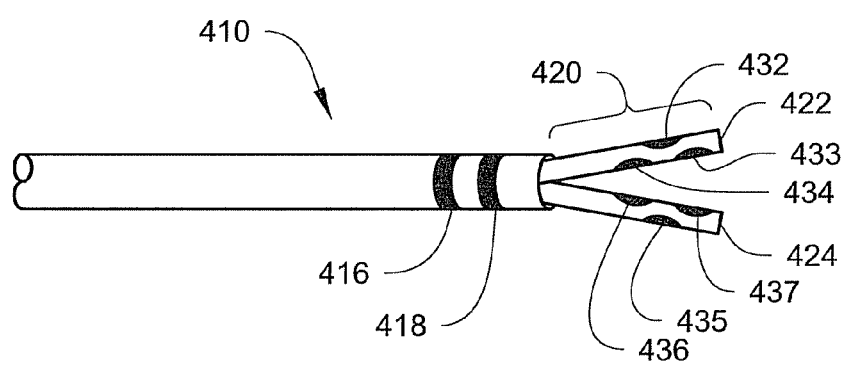
FIG. 15 depicts another exemplary embodiment of a delivery device with a capture device extending out of a delivery lumen in the delivery device.

Another potential embodiment depicted in FIG. 15 includes ring electrodes 416 and 418 on the delivery device 410. The electrodes 433, 434, 436, and 437 on the internal surfaces of the jaws 422 and 424 could be used to help better navigate and position the capture device 420. The external electrodes 432 and 435 on the external surfaces of the jaws 422 and 424 could be used to differentiate tissue on the external surface of the jaws 422 and 424 from that in contact with the internal surfaces of the jaws. Electrodes 433 and 434 on jaw 422 and electrodes 436 and 437 on jaw 424 only capture the near-field EGM signal on the internal grasping surfaces of the jaws. External electrodes 432 and 435 may be used to determine the position of the capture device 420 relative to the pericardium, ventricular tissue underneath the LAA or any other tissue. Any or all of the electrodes could be monopolar or multipolar.

With the ability to differentiate tissue on the external surface versus the internal surface of the capture device 420, the configuration of electrodes on the capture device 420 may provide additional specificity of EGM interpretation versus the configuration seen in the device of FIG. 14. The ring electrodes 416 and 418 on the delivery device 410 could again be used for navigation in the pericardial space in a similar manner as described for similar arrangements herein (with the potential for a more precise near-field EGM read from the two ring electrodes 416 and 418).

Figure 16:
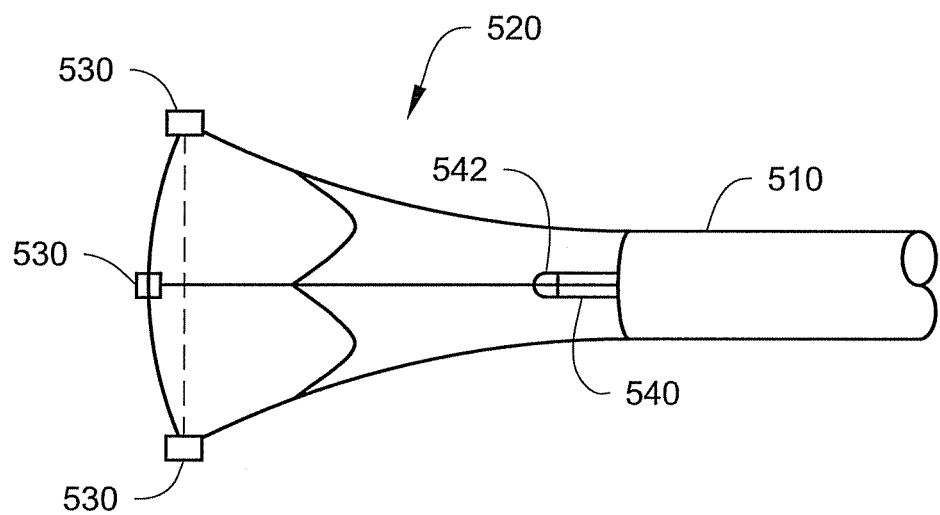
FIG. 16 depicts another exemplary embodiment of a delivery device with a capture device and a guiding element extending out of a delivery lumen in the delivery device.

In addition to the examples described herein, navigation and tissue capture systems described herein may be integrated into known tissue capture systems. Examples of some potentially suitable tissue capture systems including delivery devices and capture devices may be described in U.S. Patent Application Publication No. US 2007/0073313 (Liddicoat et al.). One example (depicted in FIG. 16) of a capture device 520 according to the principles described in Liddicoat et al. may, for example, include electrodes 530 integrated with the supports or guides included in the disclosed devices. The capture device 520 may preferably be delivered using a delivery device 510. The system of FIG. 16 may also include an optional guide element 540 which may include an electrode 542 in place of or in addition to a magnet as described in Liddicoat et al. If the guiding element 540 is provided with an electrode 542, the electrodes 530 on the capture device 520 may be optional.

Figure 17:
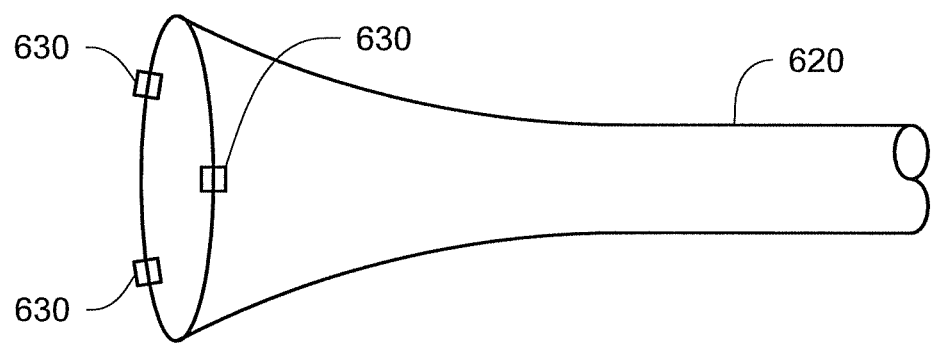
FIG. 17 depicts another exemplary embodiment of a capture device.

Yet another exemplary embodiment of a capture device 620 is depicted in FIG. 17 in the form of a catheter that includes a lumen that may be used to provide suction to capture tissue. The capture device 620 may include one or more electrodes 630 proximate (at or near) the distal end of the catheter to detect physiological electrical activity to guide the capture device as described herein. The capture device 620 may also (or alternatively) include one or more electrodes that are spaced from the distal end of the capture device 620 as described herein with respect to, e.g., the embodiments depicted in FIGS. 18-20.

Figure 18:
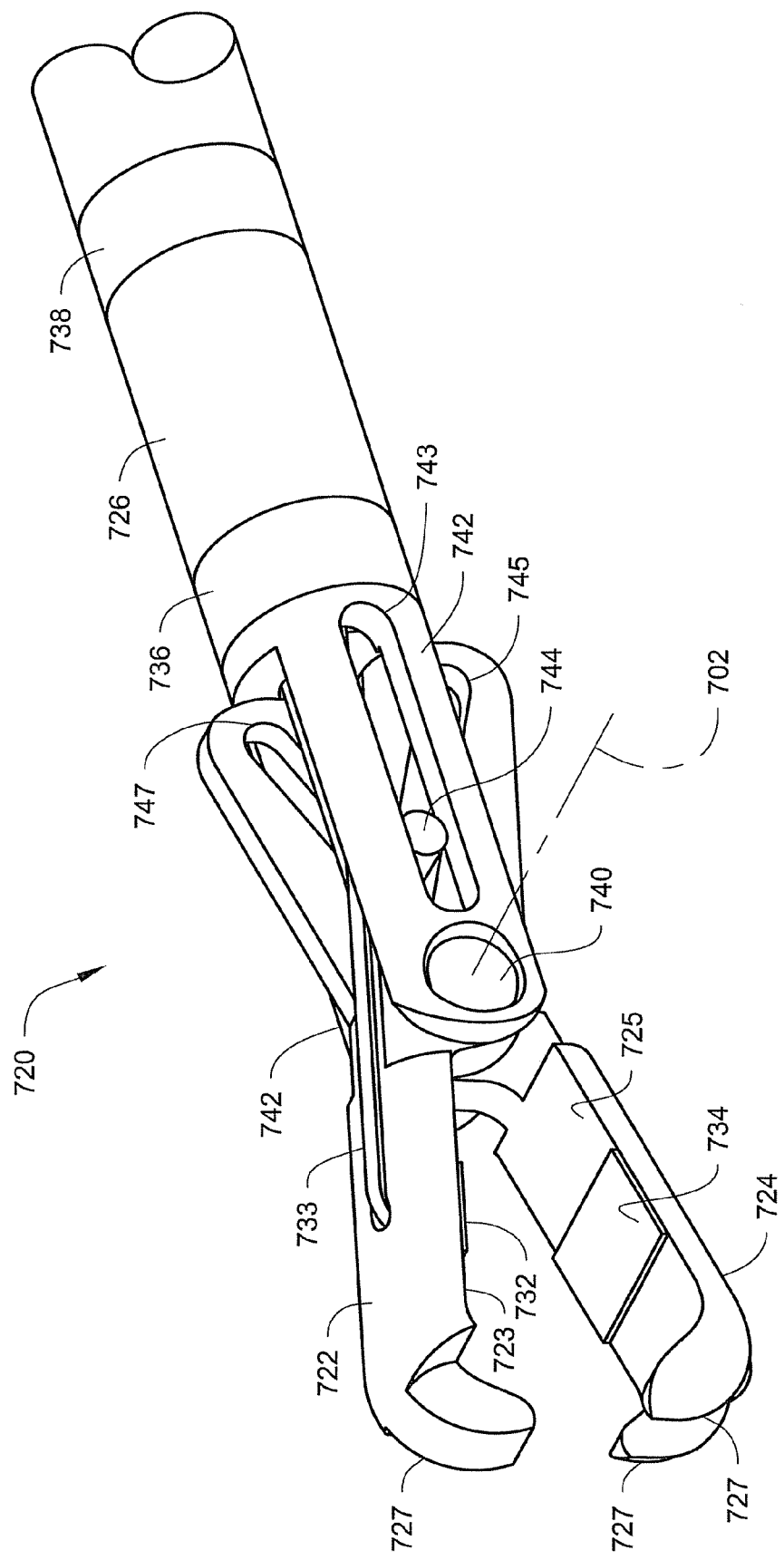
FIG. 18 is an enlarged perspective view of the distal end portion of one embodiment of a capture device in an open configuration.

Still another exemplary embodiment of a capture device 720 that may be used in the systems and methods described herein is depicted in connection with FIG. 18. The capture device 720 includes a first jaw 722 and a second jaw 724. The first and second jaws 722 and 724 may be mounted on the distal end of a capture shaft 726 that can be used to advance the capture device 720 through the lumen of an introducer, endoscope, catheter, trocar, etc. that can provide access to a selected internal body location.

The capture devices of systems and methods described herein may preferably operate in an atraumatic manner to capture tissue. As used herein, "atraumatic" (and variations thereof) means that the capture devices described herein, when used to capture tissue, do not cut, sever, or remove the captured tissue. In other words, the capture devices used in connection with the systems and methods described herein can be distinguished from conventional biopsy devices because the capture devices described herein preferably do not cut, sever, and/or remove of tissue as would conventional biopsy devices. The capture devices may, however, include retention structures/features such as serrations, teeth, roughened surfaces, posts, pins, adhesives, etc. that contribute to the ability of the capture devices to maintain attachment to tissue captured within the jaws while still remaining an atraumatic device.

In the depicted embodiment of the capture device 720, one example of a retention structure is found in the complementary teeth 727 found on the jaws 722 and 724. The depicted retention structure includes one tooth 727 located on the first jaw 722 and two teeth 727 located on the second jaw 724. The tooth 727 on jaw 722 may preferably nest within the pair of teeth 727 to assist in retaining tissue within the capture device 720.

The first jaw 722 of capture device 720 has an interior surface 723 that faces the interior surface 725 of the opposing second jaw 724. Also included in the depicted embodiment of capture device 720 is a first electrode 734 positioned on the interior surface 723 of the first jaw 722 and a second electrode 736 positioned on the interior surface 725 of the second jaw 724.

As described herein, the capture device 720 may have a closed configuration in which the jaws are closed such that the interior surfaces 723 and 725 of the first and second jaws 722 and 724 move towards each other and an open configuration (see, e.g., FIG. 18) in which the first and second jaws are open and spaced apart such that the capture device can capture tissue between the jaws 722 and 724.

The capture device may optionally include a mechanism to lock the jaws in the closed configuration such that a user is not required to continually hold the capture device 720 in the closed configuration. The locking mechanism may preferably be operable from the proximal end of the capture device. In one embodiment, the locking mechanism may take the form of a biased (e.g., spring-loaded, etc.) mechanism that holds the jaws of the capture device in a closed configuration in the absence of any intervening force that is applied to open the jaws. Such an embodiment may be referred to as having "normally-closed" jaws.

In still other embodiments, the jaws of a capture device may alternatively be biased (e.g., spring-loaded, etc.) in an open configuration in the absence of an intervening force that is applied to close the jaws. Such an embodiment may be referred to as having "normally-open" jaws. Such jaws may be closed to capture tissue using any suitable mechanism including, but not limited to a sheath that can be advanced distally over the jaws, thereby urging them into a closed configuration.

Referring to, e.g., FIG. 1 in addition to FIG. 18, the capture device 720 may also have a delivery configuration in which the distal end of the capture device 720 (typically the jaws 722 and 724) is contained within the capture lumen of a delivery device such as a sheath, introducer, endoscope, catheter, trocar, etc. The capture device may further have an extended configuration in which the distal end of the capture device 720 extends out of the capture lumen of a delivery device proximate the distal end of the delivery device. This concept is also described above in connection with FIG. 1.

In the depicted embodiment, the jaws 722 and 724 are both attached for rotation about an axis 702 that is oriented generally transverse to a longitudinal axis 701 that extends from a proximal end to a distal end of the capture shaft 726. The axis of rotation 702 about which the jaws 722 and 724 rotate may not necessarily be exactly transverse to the longitudinal axis 701 in any or all planes that contain the longitudinal axis 701.

Figure 19:
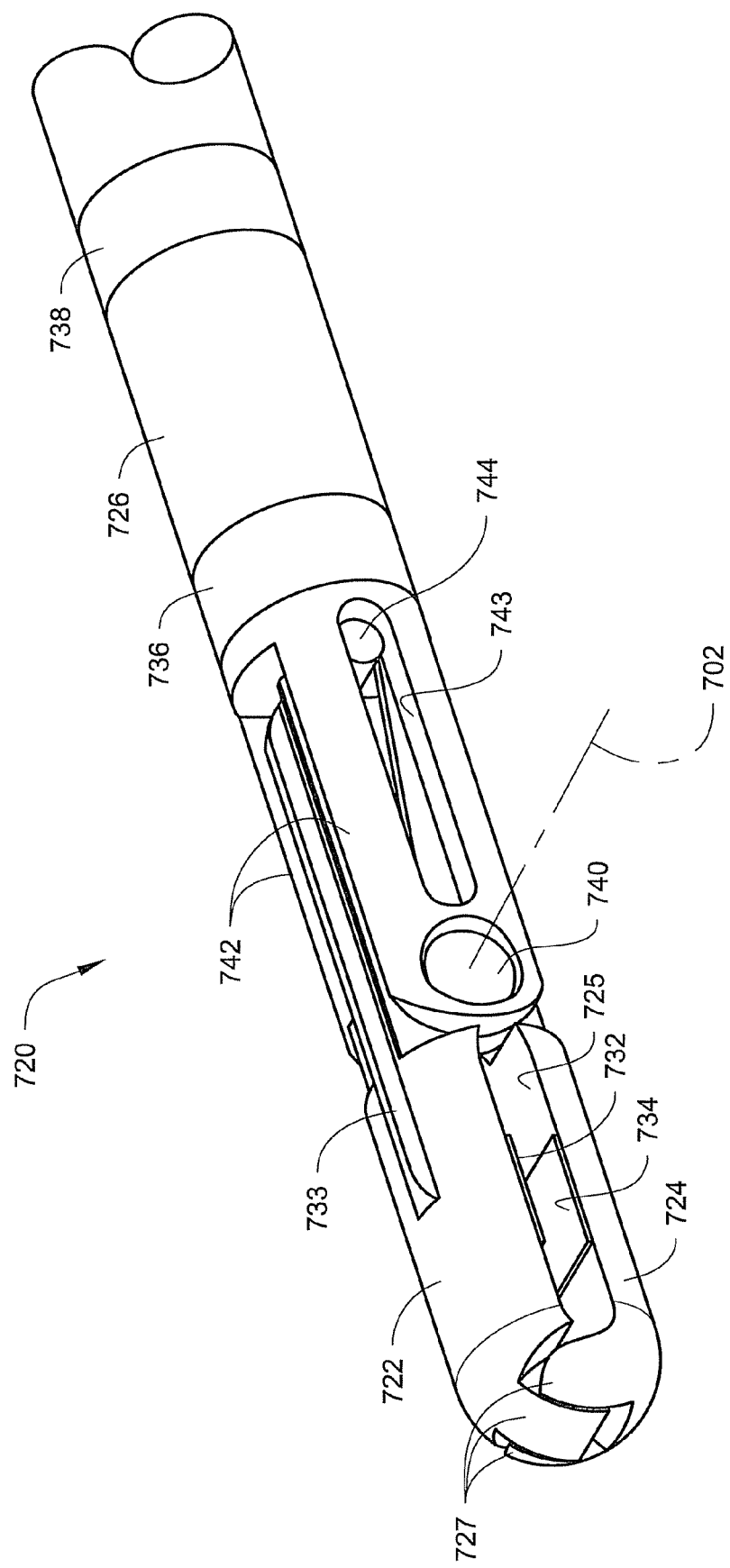
FIG. 19 is an enlarged perspective view of the capture device of FIG. 18 in a closed configuration.
Figure 20:
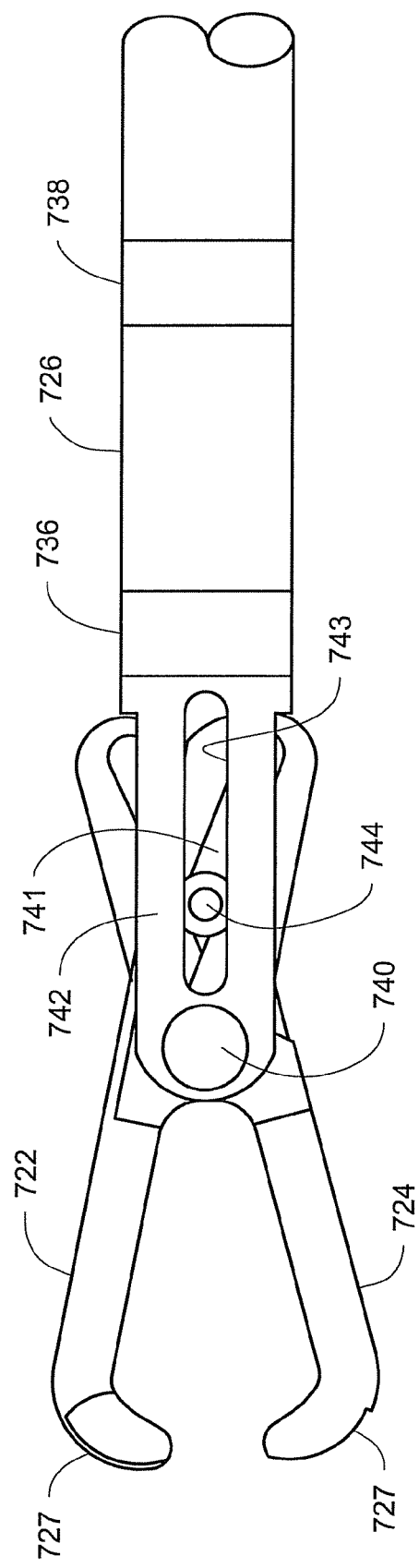
FIG. 20 is a side elevational view of the capture device of FIG. 18.

Movement of the jaws 722 and 724 between the open and closed configurations can be accomplished by a wide variety of different mechanisms. FIGS. 18-20 depict only one example of a potentially suitable mechanism. In the depicted embodiment, rotation of the jaws 722 and 724 about the axis 702 means that the jaws 722 and 724 are pivotally mounted on a main rivet 740 that extends through arms 742 that extend from the capture shaft 726. Axis 702 (about which the jaws 722 and 724 rotate) preferably extends through the main rivet 740.

Rotation of the jaws 722 and 724 about the axis 702 is effected in the depicted embodiment by moving a link rivet 744 through slots 743 formed in arms 742. Movement of the link rivet 744 is effected, in the depicted embodiment, by moving an actuator such as a drive rod 741 through an actuator lumen in the capture shaft 726, with the link rivet 744 being attached to the drive rod 741. The link rivet 744 also extends through slots 745 and 747 located in the jaws 722 and 744. As the link rivet 744 is advanced distally towards the distal end of the capture device 720 (see, e.g., FIGS. 18 and 19), the jaws 722 and 724 open. Conversely, as the drive rod 741 and attached link rivet 744 are moved proximally, the jaws 722 and 724 close (see, e.g., FIG. 20).

The capture device 720 also includes a variety of electrodes that can be used to monitor EGM signals. The depicted embodiment of the capture device 720 includes a first electrode 732 located on the interior surface 723 of the first jaw 722 and a second electrode 734 located on the interior surface 725 of the second jaw 724.

A first electrode lead 733 extends from the first electrode 732 towards a proximal end of the capture device 720. The first electrode lead 733 is connected to the electrode 732, in the depicted embodiment, through the jaw 722 with a similar lead being located on the second jaw 724 (but not depicted in FIGS. 18 and 19). The leads may preferably extend through the capture shaft 726 where they terminate at an EGM monitoring apparatus connector (not seen).

A potential alternative structure for electrically connecting the electrodes 732 and 734 without using separate and discrete leads as seen in FIGS. 18 and 19 may include placing the main rivet 740 in electrical communication between a coil (other conductor) extending through the capture shaft 726, the first jaw 722, and electrode 732. The main rivet 740 is preferably electrically isolated from the second jaw 724 and its electrode 734 by any suitable technique, e.g., insulating washers, bushings, etc. (which may be constructed of dielectric materials such as, e.g., polyimides, PEEK, etc.). Similarly, the link rivet 744 may serve as the path for electrical communication between another lead (such as the drive rod 741), the second jaw 724, and electrode 734. The link rivet 744 may also be electrically isolated from the first jaw 722 and its electrode 732 by any suitable technique, e.g., insulating washers, bushings, etc. (which may be constructed of dielectric materials such as, e.g., polyimides, PEEK, etc.).

Although the jaws 722 and 724 may be made of electrically conductive materials (such as, e.g., metals, etc.), they may be coated with nonconductive materials such that, e.g., the electrodes 732 and 734 on selected surfaces, e.g., the outer surfaces, etc. Some potentially suitable nonconductive materials may include polymers, paints, epoxies, etc. Insulating the outer surfaces and other areas of the capture devices may potentially enhance the ability of the system to capture and/or distinguish EGM signals of tissue located within the capture device. In some embodiments, the electrodes provided on the capture devices may be in the form of discrete electrodes that are attached to the capture device (e.g., a jaw, etc.) as depicted in, e.g., FIGS. 18-19. Where the capture device elements on which the electrodes are placed are electrically conductive, the electrodes may be electrically isolated from the capture device.

The electrodes 732 and 734 may, in some embodiments, be located on the interior surfaces 723 and 725 of the jaws 722 and 724 such that the electrodes are located opposite from each other. In such a configuration, closure of the jaws 722 and 724 in the absence of tissue or other material located therein may preferably result in electrical communication between the electrodes, e.g., the electrodes 732 and 734 may "short out" when the jaws 722 and 724 are closed. Such an event may be useful for providing an indication to a user that not tissue has been captured by the capture device 720.

Another optional feature that may be described in connection with the embodiment of the capture device 720 depicted in FIGS. 18 and 19 is that the electrodes used on the jaws of the capture device 720 may occupy substantial portions of the interior surfaces of the jaws. For example, it may be preferred that the electrodes 732 and/or 734 occupy about one quarter or more of the interior surfaces 723 and 725 of the jaws. In some embodiments, it may be further preferred that at least one of the electrodes provided on the interior surface of a jaw occupy about one half or more of the interior surface of the jaw.

Although the capture device 720 includes a pair of electrodes, with one electrode located on each jaw, it should be understood that that many different electrode configurations are possible. For example, only one electrode may be provided such that, e.g., only one of the jaws carries an electrode (with a return electrode located elsewhere, e.g., on the capture shaft, an exterior surface of one of the jaws, on a delivery device, etc.). In some embodiments, for example, an electrode is coupled to the interior surface of a first jaw and the interior surface of a second jaw is free of any electrodes.

In another example, two or more electrodes may be placed on one jaw (on, e.g., the interior surface of the jaw), while the other jaw contains no electrodes. The two or more electrodes may be provided in any suitable configuration, e.g., they may be arranged along a straight line, in a circle, randomly, etc. An example of an embodiment in which only one of the jaws carries electrodes may be seen with reference to FIG. 15 where the capture device 420 may be provided with only one set of interior electrodes (e.g., only electrodes 433 and 434, but not electrodes 436 and 437). In such an embodiment, the opposing interior surface of the opposing jaw may be electrically conductive such that closure of the jaws places the two electrodes in electrical communication with each other (i.e., shorts out the electrodes) to provide an indication that no tissue is captured between the jaws. The electrically conductive interior surface may be inherent in the opposing jaw (if, e.g., the interior surface was exposed metal or some other conductive material) or the opposing interior surface may be provided with a conductive element on its interior surface that is placed to provide the desired shorting out function.

Still another optional feature depicted in connection with, e.g., the capture device 720 depicted in FIGS. 18-20 is the use of electrodes on the capture shaft 726. As seen in FIGS. 18 and 19, the capture shaft 726 includes a pair of shaft electrodes 736 and 738. The shaft electrodes 736 and 738 may be used to, e.g., monitor the type of tissue in contact with the shaft 726. As discussed herein, the EGM signals picked up by electrodes used with the capture devices described herein can be useful in determining the location of the device within, e.g., the pericardial space. For example, the shaft electrode(s) 726 may potentially be used in the same manner as the external electrodes on capture devices described in connection with FIGS. 4-13.

The shaft electrodes 736 and 738 may or may not be provided in the form of ring electrodes that extend around the perimeter of the shaft 726. The electrodes 736 and 738 may preferably be electrically isolated from the remainder of the capture device 720 and be placed in electrical communication with EGM monitoring apparatus through leads that extend proximally through the capture shaft 726.

Although two shaft electrodes 736 and 738 are depicted in connection with the capture device 720, the capture devices may be provided with only one shaft electrode, three or more shaft electrodes, and even no shaft electrodes. If provided, the one or more shaft electrodes may preferably be located within a distance of about 10 centimeters (cm) or less, about 5 cm or less, or even about 2 cm or less from the distal end of the capture device such that the EGM signals detected using the shaft electrodes are those that are indicative of the tissue proximate the working portion of the capture device.

The function of the shaft electrodes may, in some instances be provided and/or supplemented by using one or more electrodes at other locations, e.g., electrodes located on a delivery device used to deliver the capture device, electrodes on exterior surfaces of the jaws or any other element of any other capture device, electrodes on the skin or at other locations on the subject, etc.

Although the capture devices depicted in FIGS. 18-20 and elsewhere herein include two jaws, both of which may be moved to change between an open and closed configuration, it should be understood that the captured devices may include more than two jaws, e.g., three, four or more jaws. In still other variations, one or more of the jaws may be stationery while one or more of the remaining jaws moves to changed between the open and closed configurations. For example, with respect to the embodiment of FIGS. 18-20, the jaw 722 may be stationary with respect to the capture shaft 726, while jaw 724 rotates to move the capture device between the open and closed configurations.

As described herein, other navigation techniques may be used in combination with EGM-based navigation. An exemplary embodiment of an additional method of navigating a device to an anatomical structure (e.g., the left atrial appendage) may include delivering a device into an anatomical space (e.g., the pericardial sac); injecting image enhancement liquid (e.g., a liquid contrast agent in the case of fluoroscopy, echogenic liquids for use in conjunction with ultrasonic imaging, etc.) into the anatomical space (e.g., the pericardial sac); and identifying the location of the device and/or the locations of anatomical structures (e.g., the left atrial appendage) using any appropriate imaging modality, e.g., fluoroscopic visualization, MRI, CT scanning, etc. In some embodiments, this method and apparatus used to perform it could be used alone, i.e., without the aid of EGM-based navigation.

Although this method of navigating a device to an anatomical structure may be utilized for many anatomical structures (e.g., any structure relating to the epicardial surface of the heart such as various veins and arteries, fat pads, structural defects, etc.), the following description, for simplicity, describes the use of the method and device for navigating to and/or outlining the left atrial appendage (LAA).

Figure 21:
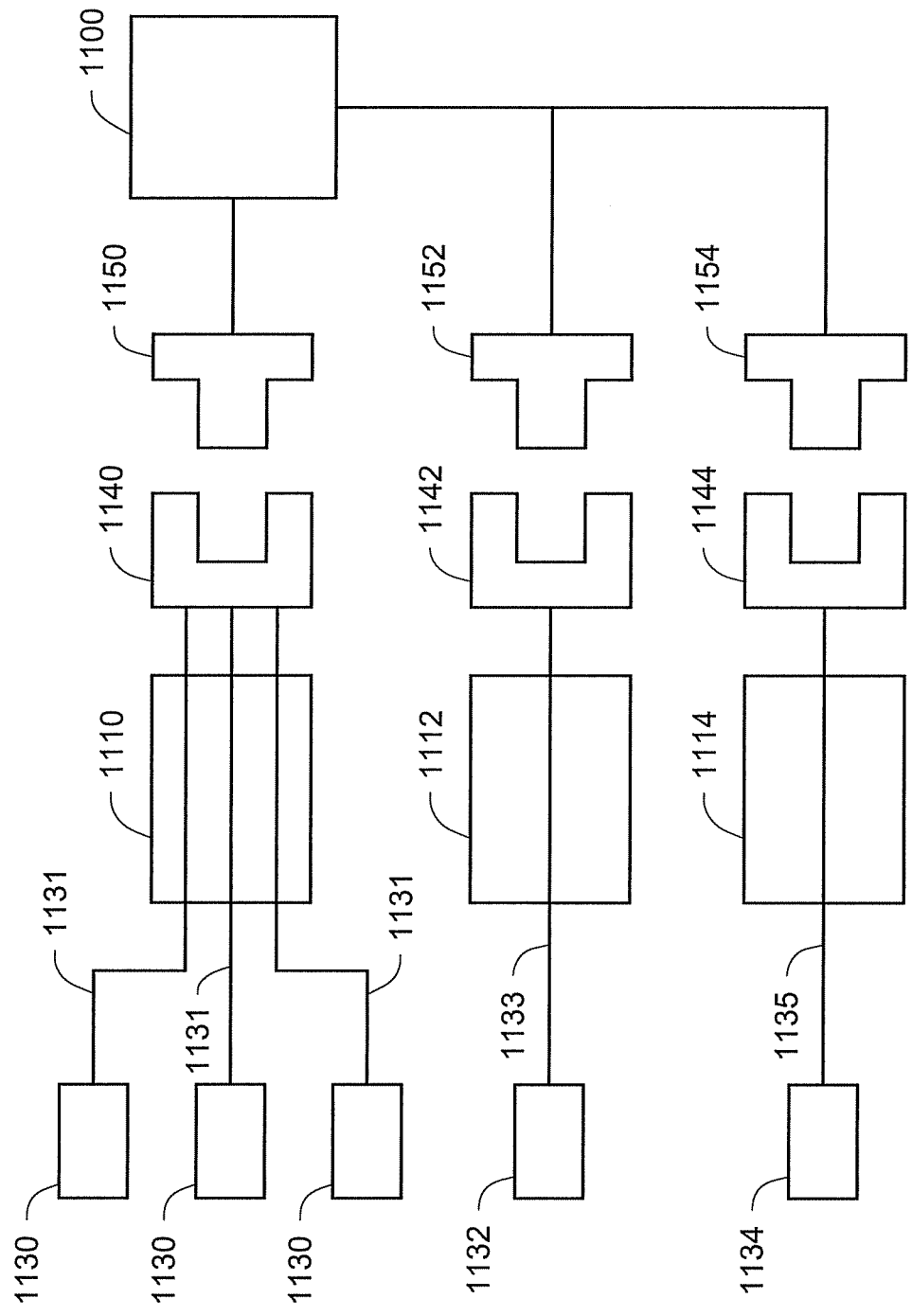
FIG. 21 is a schematic of one system including electrodes operably coupled to an electrical activity (e.g., EGM) monitoring device.

A system level schematic is depicted in FIG. 21 to show potential connections between electrodes and other components that may be used with systems described herein. The depicted system includes a capture device 1110 having one or more electrodes 1130 and connector 1140 connected to the electrodes 1130 through leads 1131. The depicted system optionally also includes a delivery device 1112 that may include an electrode 1132 (or more than one electrode) and a connector 1142 connected to the electrode 1132 through a lead 1133. The system further optionally includes ligation element 1114 that may include a ligation element electrode 1134 (or more than one electrode) and a connector 1144 connected to the electrode 1134 through a lead 1135. For example, the ligation element 1114 may be configured to ligate body tissue (e.g., the LAA)

The connectors 1140, 1142, and 1144 may be adapted to connect to an electrical (e.g., EGM, etc.) monitoring apparatus 1100 through connectors 1150, 1152, and 1154. As a result, innate electrical signals that may be detected by the electrodes may be monitored, displayed, analyzed, filtered, stored, manipulated, enhanced, etc. to assist a user in navigating the delivery device and/or capture device as described herein. The connectors may take any suitable form, e.g., plugs, sockets, bare wires, snap-fit connectors, etc.

Systems and/or methods described herein may be used to capture and/or to occlude body tissue, e.g., the LAA. Navigation of the capture and/or ligation devices may be performed using various characteristics of the body tissue being captured. For example, the impedance of body tissue (e.g., the LAA) may be different when such body tissue is compressed, captured, ligated, traumatized, etc. These impedance changes can potentially be used as the basis for navigating to and/or capturing selected tissue. The impedance differences can also be used in some systems and methods to control the forces exerted on the selected tissue by capture and/or ligation devices. As the tissue is compressed during capture or ligation it will typically experience ischemia which may result in a corresponding changes in impedance of the tissue. In some embodiments, the impedance characteristics of tissue subjected to forces by a capture device and/or ligation element may provide insight as to whether or not the force is clinically safe or potentially puts the patient at risk.

Figure 22:
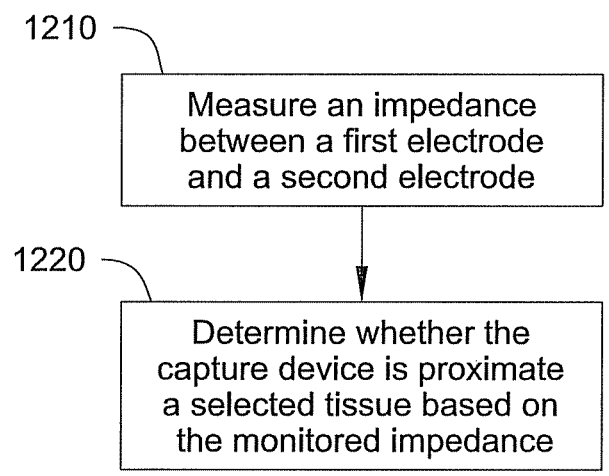
FIG. 22 is a block diagram of a method and configuration to be used with the systems described herein.

FIG. 22 can be used to describe one configuration and method of utilizing the systems described herein (e.g., the system described with reference to FIGS. 1-21) that may use the impedance of body tissue for navigation, capture, and/or occlusion control as discussed herein. As shown, electrical monitoring apparatus (e.g., electrical monitoring apparatus 1100) may be configured to: monitor an impedance between a first electrode and a second electrode (e.g., electrodes 1130, 1132) (block 1210); and determine whether a capture device (e.g., capture device 1110) is proximate a selected tissue (e.g., atrial tissue, ventricular tissue, etc.) based on the monitored impedance (block 1220). Although described above as confirming that a selected type of tissue has been captured, in some embodiments measured impedance may be used to exclude certain tissues rather than confirm capture. For example, fat may have an extremely high impedance and myocardium may have a much lower impedance. In such a case, although a user may not be able to differentiate between different types of myocardium, the user may be able to determine that epicardial fat has not been captured. As a result, measured impedance could be used to exclude certain types of tissue rather than be certain of inclusion of different types of tissue.

At least in one embodiment, the capture device used in connection with electrical monitoring apparatus 1100 may include a first jaw and a second jaw where the first jaw and the second jaw include an open configuration in which the first jaw and the second jaw are open and a closed configuration in which the first jaw and the second jaw are closed (e.g., the interior surface of the first jaw is located closer to an interior surface of the second jaw when the first jaw and the second jaw are in the closed configuration than when the first jaw and the second jaw are in the open configuration). Further, the first electrode may be coupled to the interior surface of the first jaw and the second electrode may be coupled to the interior surface of the second jaw (e.g., the electrodes face one another in at least one configuration).

When capturing and/or ligating body tissue (e.g., the LAA), the electrical activity of the body tissue may exhibit variations, which may be consistent with compression, ischemia and/or trauma of the body tissue (e.g., in the case of LAA capture, a small ST segment elevation may exist). Further, a substantial decrease in the electrical activity of the body tissue may indicate that the body tissue is sufficiently ligated to, in the case of, e.g., the left atrial appendage, limit flow of blood into the appendage.

In some embodiments, the impedance of tissue (e.g., the left atrial appendage) being occluded may provide an indication as to the forces applied to the tissue. In some embodiments, a threshold value may be obtained during the procedure itself in the form of a baseline value, with subsequent measurements being compared to the (baseline) threshold to determine when the differential between a current measurement and the threshold value exceeds a predetermined limit, then an indication can be made that occlusion is sufficient, etc.

In some embodiments, the absolute value of the measured impedance may be dependent on a variety of factors such as, e.g., the size of the patient, the size of any reference electrodes/patches that are being used, etc. As such, absolute measurements may be of less importance than the changes in the impedance values over time. Changes in measured impedance during the occlusion process (e.g., from the start of occlusion to the end), as discussed herein, may provide an indication that occlusion has reached a selected limit. Such changes in impedance may occur during occlusion as a result of, e.g., extra-cellular fluid accumulation due to cell death or cell rupture, etc. In some embodiments, an increase in measured impedance of the tissue being occluded of, e.g., 15% or more, 25% or more, etc. may be used as an indication that sufficient occlusion has been obtained and, thus, occlusion should be halted.

Lack of electrical activity in the captured and/or ligated tissue (e.g., the lack of EGM signals on the distal tip of the left atrial appendage) may be used to confirm that the tissue (e.g., the left atrial appendage) is ischemic, at which point the process can be halted to, e.g., prevent over-tightening. If the tissue, such as the left atrial appendage is being occluded during pacing, pacing capture may be lost when tissue becomes ischemic due to the occlusion forces. In some embodiments, the time between starting occlusion and when complete occlusion and, thus, loss of pacing capture occurs is relatively brief. This change can, however, be useful if, during occlusion, the system is configured to determine when the EGM signal decreases be a predetermined or threshold value (e.g., 10%, 20%, 30%, etc.) and the pacing capture threshold increases by a predetermined or threshold value (e.g., 10%, 20%, 30%, etc.) and/or pacing is lost. At that point, i.e., a decrease in EGM signal coupled with an increase in pacing capture threshold (and/or loss of pacing capture), the system may be configured to make a determination that occlusion is sufficient and no further occlusion should be performed. These measurements may further be correlated with measured impedance of the captured tissue (as discussed herein) as a further indication that sufficient occlusion has been performed.

In some embodiments, the left atrial appendage may appear to have residual flow using another monitoring technique (e.g., Trans-Esophageal Echo (TEE), Intra-Cardiac Echo (ICE), Doppler, etc.) but the EGM signals may have attenuated to near zero. In this case, the operator may have an indication that the left atrial appendage tissue has become ischemic even though the appendage has not been closed sufficiently to prevent flow. In this situation, the operator may decide to cease tightening suture any further and investigate why there is residual flow.

In some embodiments, EGM signals in the left atrial appendage may attenuate to zero at approximately the same time as the ostium closes under normal circumstances. Any variation from this could provide the basis for a determination that something out of the ordinary has occurred. If the capture device has captured annular fat then, despite tightening, there would be no decrease in the electrogram and no change in the far field electrograms being picked up. If the capture device has captured ventricular myocardium (e.g., aneurysm or diverticulum), then the large electrogram would not decrease with appendage occlusion. If the capture device has captured the appendage, but occlusion is occurring over some other structure (right atrial appendage, etc.) because the capture device had been inadvertently released and the ligature slipped to another site, then appendage electrograms will not change despite tightening.

In some embodiments, the operator could use flow detection within the appendage (e.g., TEE, ICE, Doppler, etc.) as the primary indication of closure of the appendage and then continue tightening until the EGM signals attenuate. Using both flow detection and EGM signal attenuation might prevent over tightening and accidental ripping/tearing of the left atrial appendage tissue.

At least in one embodiment, the capture device may include the first electrode and a ligation element (e.g., configured to ligate body tissue that may be captured by the capture device) that may include the second electrode with, e.g., the two electrodes being used to measure an impedance across body tissue, to measure electrical activity, etc. In such a configuration, the electrical monitoring apparatus may be further configured to determine whether the ligation element is located proximate selected tissue (e.g., atrial tissue, ventricular tissue, etc.) based on monitoring electrical activity using at least one electrode as described herein. For example, the electrical monitoring apparatus may be configured to compare the monitored electrical activity to a threshold value and determine whether the body tissue has been ligated based on the based on the comparison between the monitored electrical activity and the threshold value.

Monitoring of tissue impedance between a first electrode and a second electrode by the electrical monitoring apparatus 1100 may be performed using various techniques. For example, the electrical monitoring apparatus may be configured to monitor the impedance between a first electrode and a second electrode by monitoring the impedance at one or more selected frequencies and/or one or more selected amplitudes between the first electrode and the second electrode. Using different combinations of frequencies and amplitudes may be assist in delineating between various types of tissue. For example, the impedance of atrial tissue may respond differently at higher frequencies then ventricular tissue.

In some embodiments, determining whether the capture device and/or ligation element is proximate selected tissue based on the monitored impedance may be performed using various techniques. In other words, navigation to selected tissue such as, e.g., the left atrial appendage, may be performed by monitoring impedance of the tissue proximate selected electrodes. For example, the electrical monitoring apparatus may be configured to determine whether the capture device is proximate selected tissue based on the monitored impedance by comparing the monitored impedance to a known value, a threshold value, etc., wherein the known and/or threshold values may be acquired by monitoring the impedance of the selected tissue, or may otherwise be predetermined (e.g., historically, empirically, etc.).

As discussed herein, the monitored impedance may be used in various ways other than determining whether the capture device and/or ligation element is located proximate the selected tissue. For example, the impedance as measured by the electrical monitoring apparatus may be used as an indication of the force being applied to the selected tissue by the capture and/or ligation devices. That information may be used to control the amount of force applied by the capture and/or ligation devices. For example, a capture device may be tightened on or around body tissue during the capture process while the impedance of the tissue is being monitored to provide an indication as to the force being applied to the tissue. In some embodiments, the electrical monitoring apparatus may be configured to provide a signal to the user (e.g., through a sound, visual cue, etc.) that the body tissue has been sufficiently captured. The signal may be triggered based on the monitored impedance of the tissue, with the monitored impedance being compared to a threshold value, a known value, etc. as discussed herein. In at least one embodiment, the system may be configured to provide the signal to a user before body tissue is undesirably damaged by the application of excessive force.

Figure 23:
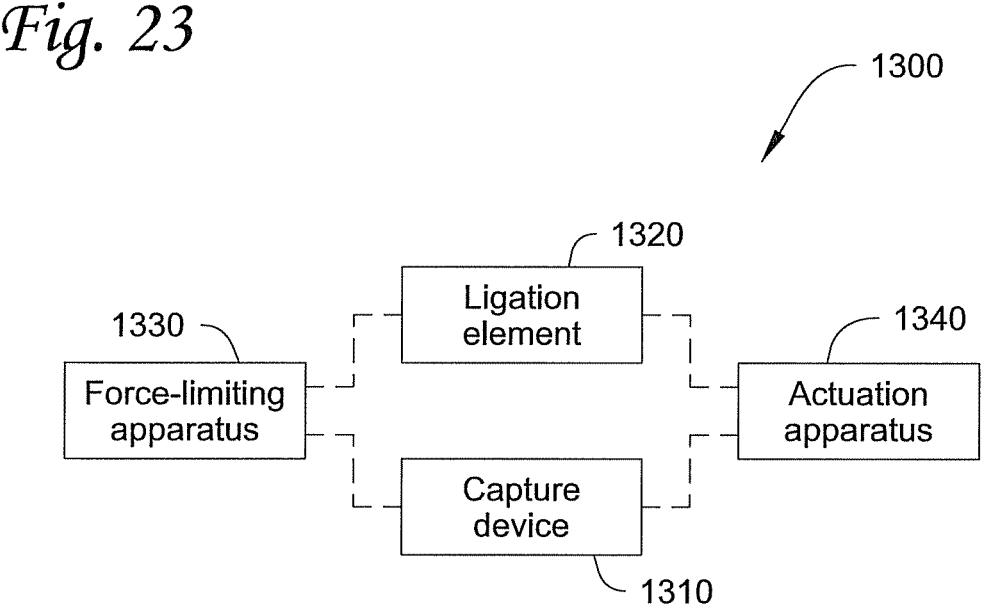
FIGS. 23-25 are block diagrams of portions of exemplary tissue capture and ligation systems.

The tissue capture systems described herein may use additional components to assist in the capture and/or occlusion of body tissue. For example, FIG. 23 depicts a portion of an exemplary tissue capture system 1300 that includes force-limiting apparatus and/or actuation apparatus. The system includes a capture device 1310 configured to capture body tissue; a capture shaft (not shown) including an elongated body including a proximal end and a distal end, wherein the distal end of the capture shaft is coupled to the capture device 1310; a ligation element 1320 configured to ligate the body tissue; and force-limiting apparatus 1330.

The force-limiting apparatus 1330 may, in some embodiments, be operably coupled to the ligation element 1320 to restrict the amount of force applied by the ligation element 1320 when the ligation element 1320 is tightened around body tissue. In some embodiments, the force-limiting apparatus 1330 may be operably coupled to the capture device 1310 to restrict the amount of force applied by the capture device 1310 to the body tissue. In still other embodiments, a force-limiting apparatus 1330 may be operably coupled to both the capture device 1310 and the ligation element 1320. The force-limiting apparatus 1330 may be found in any suitable location, i.e., proximate a capture device and/or ligation element, in a shaft carrying a capture device and/or ligation element, at a proximal end of the shaft carrying the capture device and/or ligation element (e.g., in a handle), etc.

The force-limiting apparatus 1330 may be electrically controlled (e.g., by electrical monitoring apparatus) and/or include one or more mechanical and/or electrical devices, e.g., a slip clutch, a spring, a ratchet mechanism with a force limiting pawl, etc. may be operably coupled to the ligation element 1320 and/or capture device 1310.

For example, if the capture device 1310 includes a first jaw and a second jaw, then the force-limiting apparatus 1330 may include a spring operably coupled to the first jaw and/or the second jaw such that the spring operates to keep the first jaw and the second jaw in a normally closed configuration (e.g., thereby limiting the grasping force of the capture device). Such biasing elements (e.g., springs, magnets, etc.) may be used to provide a normally-closed configuration to many different capture devices (i.e., normally closed capture devices are not limited to those including jaws. Any spring, magnet, or other biasing element that may be used to provide a normally-closed capture device may be located proximate the capture device itself and/or proximally of the capture device itself, e.g., in the shaft or at the proximal end of the shaft carrying the device (in, e.g., the handle).

In some embodiments, the force limiting apparatus may provide feedback in the form of, e.g. visual, audible, tactile, etc. alerts that signal to a user that desirable limits are being reached or have been reached. In other embodiments, the feedback may also or alternatively be automated such that, once a determination has been made that the predetermined force limits have been reached, the system may include an automated force-limiting mechanism such that no further increases in the applied force are possible.

In some embodiments, electrical monitoring apparatus may be operably coupled to the force-limiting apparatus 1330 and configured to use the force-limiting apparatus 1330 to control forces applied by the capture devices 1310 and/or the ligation elements 1320. For example, the electrical monitoring apparatus may be configured to use the force-limiting apparatus 1330 to restrict the amount of force applied by the ligation element 1320 when the ligation element 1320 is tightened around body tissue or applied by the capture device 1310 when the capture device 1310 is capturing body tissue (e.g., based on a monitored impedance as described with respect to FIG. 22).

The system 1300 may further include actuation apparatus 1340 operably coupled to the capture device 1310 and/or ligation element 1320. The actuation apparatus 1340 may be, in some embodiments, configured to actuate the capture device 1310 to capture body tissue (e.g., the LAA). The actuation apparatus 1340 may, in some embodiments, be configured to tighten and/or loosen the ligation element 1320 around body tissue (e.g., the LAA). Further, the actuation apparatus 1340 may be operably coupled to electrical monitoring apparatus, which may be further configured to actuate the capture device 1310 to capture the body tissue using the actuation apparatus 1340 and/or tighten the ligation element 1320 around the body tissue using the actuation apparatus 1340, e.g., based on a monitored impedance as described with respect to FIG. 22, monitored electrical activity, etc.

Although system 1300 depicts a single actuation apparatus 1340 and a single force-limiting apparatus 1330 in use by both the capture device 1310 and the ligation element 1320, two or more actuation apparatus 1340 and/or two or more force-limiting apparatus 1330 may be used in connection with system 1300. For example, in at least one configuration, the ligation element 1320 may be operably coupled to a first actuation apparatus and/or a first force-limiting apparatus and the capture device 1310 may be operably coupled to a second actuation apparatus and/or a second force-limiting apparatus.

Further, the connection lines, the force-limiting apparatus 1330, and the actuation apparatus 1340 as depicted in FIG. 23 are dashed representing that such connections and apparatus may be optional. For example, the system 1300 may include force-limiting apparatus 1330 operably coupled to only the ligation element 1320 and not include an actuation apparatus 1340. Further, for example, the system 1300 may include force-limiting apparatus 1330 operably coupled to both of the ligation element 1320 and the capture device 1310 and actuation apparatus 1340 only operably coupled to the capture device 1310.

Figure 24:
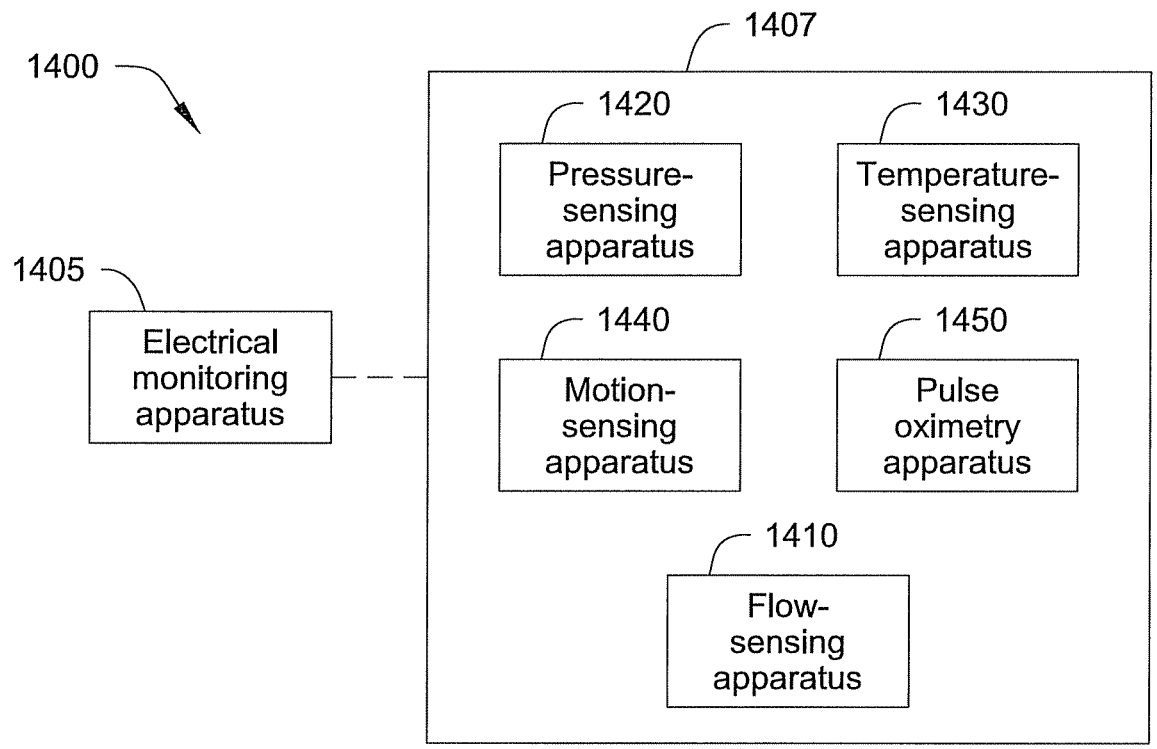

FIG. 24 depicts a portion of another exemplary tissue capture system 1400. The system 1400 may include a capture device (not shown) configured to capture body tissue as described herein; a capture shaft (not shown) including an elongated body including a proximal end and a distal end, wherein the distal end of the capture shaft is coupled to the capture device; electrical monitoring apparatus 1405; and one or more optional sensor apparatus 1407 that may be operably coupled to the electrical monitoring apparatus 1405. The one or more sensor apparatuses 1407 may be used to sense or monitor one or more different characteristics that may be used for navigation, capture, and/or force control of selected tissue. As depicted in FIG. 24, the system includes flow-sensing apparatus 1410, pressure-sensing apparatus 1420, temperature-sensing apparatus 1430, motion-sensing apparatus 1440, and pulse oximetry apparatus 1450. Although not depicted in FIG. 24, the sensor apparatus 1407 may also include one or more electrodes that can be used to measure impedance or other electrical characteristics as discussed herein.

The flow sensing apparatus 1410 may be operably coupled to the capture device such that the electrical monitoring apparatus 1405 may use the flow-sensing apparatus 1410 to measure fluid flow within the captured tissue (e.g., within the left atrial appendage). The flow-sensing apparatus 1410 may include one or more flow sensors (e.g., Doppler probes) mounted either directly on the capture and/or ligation devices and appropriate apparatus needed to detect fluid flow using the flow sensors. If, during occlusion, the sensed fluid flow abruptly decreases and/or reaches zero, the system can be configured to make a determination that occlusion has been completed. Flow sensing may be used in combination with one or ore other techniques described herein to address those situations in which, for example, the flow-sensing apparatus is measuring flow in a volume that is not being occluded (e.g., in a neighboring vessel, etc.) and occlusion is complete, but the flow-sensing apparatus is still indicating the presence of fluid flow despite occlusion.

The pressure-sensing apparatus 1420 may be operably coupled to the capture device such that the electrical monitoring apparatus 1405 may use the pressure-sensing apparatus 1420 to measure the amount of pressure applied by the capture device, e.g., to body tissue. The pressure sensing apparatus 1420 may include one or more pressure sensors mounted either directly on the capture and/or ligation devices and appropriate apparatus needed to detect pressure using the pressure sensors.

For example, in the embodiment in which the capture device includes a first jaw and a second jaw, the pressure-sensing apparatus 1420 apparatus may include sensors operably coupled to the first jaw and/or the second jaw so as to measure the pressure applied between the first jaw and the second jaw. Such pressure measurement may be useful to apply a sufficient amount of "grasping" force with the capture device to capture a selected body tissue (e.g., the LAA).

The electrical monitoring apparatus 1405 may be configured to compare the monitored pressure applied by the capture device to a threshold value and determine whether the body tissue is captured by the capture device based on the comparison between the monitored pressure and the threshold value. Further, for example, if the pressure is below a predetermined threshold value, then it may be desirable to increase the force applied by the capture device to assist the capture device in holding position so that it is less likely to dislodge from or release the captured tissue during subsequent procedures. If the pressure is above a predetermined threshold value, it may be desirable to decrease the pressure applied by the capture device to, e.g., limit or prevent trauma of the captured body tissue.

The electrical monitoring apparatus 1405 may be further configured to report to a user the amount of pressure applied by the capture device and record the pressure applied by the capture device to, e.g., provide guidance to a user.

Further, the monitored pressure may be used to limit the amount of force applied by the capture device and/or a ligation element using a force-limiting apparatus 1330 as described herein with reference to FIG. 23. In at least one embodiment, the force-limiting apparatus 1330 may be operably coupled to the pressure sensing apparatus 1420 (e.g., through the electrical monitoring apparatus 1405) and to the capture device and/or ligation element to restrict the amount of force/pressure applied by the capture device and/or ligation element to the body tissue.

In some embodiments, the monitored pressure may be used to control an actuation apparatus 1340 as described herein with reference to FIG. 23. In at least one embodiment, the actuation apparatus (not shown) may be operably coupled to the pressure sensing apparatus 1420 (e.g., through the electrical monitoring apparatus 1405) and to the capture device and/or ligation element to restrict the amount of force/pressure applied by the capture device and/or ligation element to the body tissue by controlling the actuation apparatus itself. In some embodiments, the actuation apparatus may be configured to actuate the capture device to capture the body tissue based on the amount of pressure applied by the capture device as monitored by the pressure-sensing apparatus 1420. In some embodiments, the actuation apparatus may be configured to operate the ligation element based on the amount of pressure applied by the capture device as monitored by the pressure-sensing apparatus 1420.

Also depicted in FIG. 24, the system may include temperature-sensing apparatus 1430. The temperature-sensing apparatus 1430 may be operably coupled to the capture device such that the electrical monitoring apparatus 1405 may use the temperature-sensing apparatus 1430 to measure the temperature of the body tissue captured by the capture device. The temperature sensing apparatus 1430 may include one or more temperature sensors mounted either directly on the capture and/or ligation devices and appropriate apparatus needed to detect temperature of tissue using the temperature sensors.

For example, in the embodiment in which the capture device includes a first jaw and a second jaw, the temperature-sensing apparatus 1430 apparatus may include temperature sensors operably coupled to the first jaw and/or the second jaw so as to measure the temperature of tissue in contact with the temperature sensors. In other embodiments, the temperature-sensing apparatus may be provided in the form of, e.g., infrared temperature sensors with the infrared sensors located at any appropriate location on the capture devices, ligation devices, and/or devices used to deliver the capture and/or ligation devices.

In some embodiments, temperature of body tissue (e.g., the LAA) may change depending whether the body tissues is being grasped, ligated, etc. As such, the electrical monitoring apparatus 1405 may be configured to report the monitored temperature to a user. The electrical monitoring apparatus 1405 may be further configured to compare the monitored temperature to a threshold value and determine whether the body tissue is captured by the capture device based on the comparison between the monitored temperature and the threshold value. In the case of ligation control, the measured temperature may be used to determine whether the ligation is sufficient.

In situations where temperature is indicative of the forces being exerted on the tissue, if the measured temperature indicates that the pressure is below a predetermined threshold value, then it may be desirable to increase the force applied by the capture device to assist the capture device in holding position so that it is less likely to dislodge from or release the captured tissue during subsequent procedures. If the measured temperature indicates that pressure is above a predetermined threshold value, it may be desirable to decrease the pressure applied by the capture device to, e.g., limit or prevent trauma of the captured body tissue.

The electrical monitoring apparatus 1405 may be further configured to report to a user the temperatures measured by the capture device and record the temperature measured by the capture device to, e.g., provide guidance to a user.

Further, the measured temperature may be used to limit the amount of force applied by the capture device and/or a ligation element using a force-limiting apparatus 1330 as described herein with reference to FIG. 23. In at least one embodiment, the force-limiting apparatus 1330 may be operably coupled to the temperature sensing apparatus 1430 (e.g., through the electrical monitoring apparatus 1405) and to the capture device and/or ligation element to restrict the amount of force/pressure applied by the capture device and/or ligation element to the body tissue.

In some embodiments, the measured temperature may be used to control an actuation apparatus 1340 as described herein with reference to FIG. 23. In at least one embodiment, the actuation apparatus (not shown) may be operably coupled to the temperature sensing apparatus 1430 (e.g., through the electrical monitoring apparatus 1405) and to the capture device and/or ligation element to restrict the amount of force/pressure applied by the capture device and/or ligation element to the body tissue by controlling the actuation apparatus itself. In some embodiments, the actuation apparatus may be configured to actuate the capture device to capture the body tissue based on the temperature as monitored by the temperature sensing apparatus 1430 (which, as discussed herein, may be indicative of the amount of pressure applied by the capture device). In some embodiments, the actuation apparatus may be configured to operate a ligation element based on the temperature of selected tissue as measured by the temperature sensing apparatus 1430.

Also depicted in FIG. 24, the system may include motion-sensing apparatus 1440. The motion-sensing apparatus 1440 may be operably coupled to the capture device such that the electrical monitoring apparatus 1405 may use the motion-sensing apparatus 1440 to detect motion of tissue captured by the capture device. The motion-sensing apparatus 1440 may include one or more motion sensors (e.g., accelerometers. etc.) mounted either directly on the capture and/or ligation devices and appropriate apparatus needed to detect motion of tissue using the motion sensors.

For example, in the embodiment in which the capture device includes a first jaw and a second jaw, the motion-sensing apparatus 1440 apparatus may include motion sensors operably coupled to the first jaw and/or the second jaw so as to measure the motion of tissue captured by the capture device.

For example, if the LAA is captured by a capture device and is occluded at the ostium (e.g., through ligation), the motion of the capture device may be indicative of the occlusion (e.g., if the LAA is occluded, there may be less distal motion of the LAA due to a decrease in flow within the LAA, etc.). As such, the electrical monitoring apparatus 1405 may be configured to monitor the motion of the capture device (using the motion-sensing apparatus 1440) and determine whether the ligation element has ligated the body tissue based on the monitored motion of the capture device.

Ligation control may also be based on changes in the motion of the left atrial appendage because, as the left atrial appendage is ligated, it may become ischemic and the myocardium may stop contracting. The change in the beat of the left atrial appendage could be determined by monitoring acceleration and motion at the distal tip of the appendage. For example, the system may be configured to track acceleration at the distal tip of the appendage before ligation and then monitor a continual decrease in the amplitude of acceleration as the appendage is ligated. The system may be configured to make a determination that a predetermined threshold has been reached and provide an indication that sufficient occlusion has been obtained.

An alternative to monitoring motion of the left atrial appendage directly using a dedicated motion sensor, the system may be configured to determine appendage motion using, e.g., TEE, ICE, Doppler, etc. For example, there may be an algorithm that would monitor the tissue motion of the appendage prior to ligation and track the appendage motion during the occlusion process. Again, there may be a particular threshold at which the decrease in motion indicates adequate occlusion or helps reduce the likelihood of excessive forces being applied.

Also depicted in FIG. 24, the system may include pulse-oximetry apparatus 1450. The pulse-oximetry apparatus 1450 may be operably coupled to the capture device such that the electrical monitoring apparatus 1405 may use the pulse-oximetry apparatus 1450 to detect light absorption characteristics of tissue and/or fluids captured by the capture device. The pulse-oximetry apparatus 1450 may include a light transmitter and a light receiver coupled to the capture device. The transmitter is configured to direct light through tissue captured by the capture device and the receiver is configured to detect light transmitted through the tissue (preferably the light emitted by the transmitter—if any passes through the tissue).

In at least one embodiment, the electrical monitoring apparatus 1405 may be further configured to use the data from the pulse oximetry apparatus 1450 to determine the oxygen saturation of the selected body tissue. In one embodiment where the capture device includes a first jaw and a second jaw, the transmitter may be coupled to the first jaw and the receiver may be coupled to the second jaw.

The data acquired by the pulse oximetry apparatus 1450 may be useful for various procedures. Various cardiac tissues may have different oxygen saturation characteristics and their light emitting and absorption patterns may be compared to known values to confirm the type of tissue captured by the capture device. For example the LAA may have a different oxygen saturation patterns than epicardial fats (e.g., the LAA may have higher oxygen saturation patterns). Further, for example, pulse oximetry apparatus 1450 may be used to measure tissue compression (e.g., body tissue compressed by a capture device and/or a ligation element) because the pulse oximetry apparatus 1450 may measure the blood flow and/or pulsatility and oxygen saturation, which may change due to compression and/or ligation.

As such, the electrical monitoring apparatus 1405 may be further configured to determine whether the capture device has captured selected tissue based on the light received by the receiver of the pulse oximetry apparatus 1450. Also, the electrical monitoring apparatus 1405 may be further configured to compare the light received by the receiver to a threshold value to determine whether the capture device has captured the body tissue. Further, the data monitored by the pulse oximetry apparatus 1450 may be reported to a user through audio and/or visual display apparatus.

Further, the pulse-oximetry data may be used to limit the amount of force applied by the capture device and/or a ligation element using a force-limiting apparatus 1330 as described herein with reference to FIG. 23. In at least one embodiment, the force-limiting apparatus 1330 may be operably coupled to the pulse-oximetry apparatus 1450 (e.g., through the electrical monitoring apparatus 1405) and to the capture device and/or ligation element to restrict the amount of force/pressure applied by the capture device and/or ligation element to the body tissue.

In some embodiments, the pulse-oximetry data may be used to control an actuation apparatus 1340 as described herein with reference to FIG. 23. In at least one embodiment, the actuation apparatus (not shown) may be operably coupled to the pulse-oximetry apparatus 1450 (e.g., through the electrical monitoring apparatus 1405) and to the capture device and/or ligation element to restrict the amount of force/pressure applied by the capture device and/or ligation element to the body tissue by controlling the actuation apparatus itself. In some embodiments, the actuation apparatus may be configured to actuate the capture device to capture the body tissue based on the pulse-oximetry data as obtained by the pulse-oximetry apparatus 1450 (which, as discussed herein, may be indicative of the amount of pressure applied by the capture device). In some embodiments, the actuation apparatus may be configured to operate a ligation element based on the pulse-oximetry data as measured by the pulse-oximetry apparatus 1450.

In connection with any of the different measurements described herein, e.g., tissue impedance, pressure, temperature, motion, pulse-oximetry, etc., the systems and/or methods may be configured to use the actual measurements obtained by the various sensors, electrodes, etc. and/or one or more secondary characteristics of the measured value or values, e.g., rates of change, slew rates, shapes of the curves as a function of time, frequency, etc.

Figure 25:
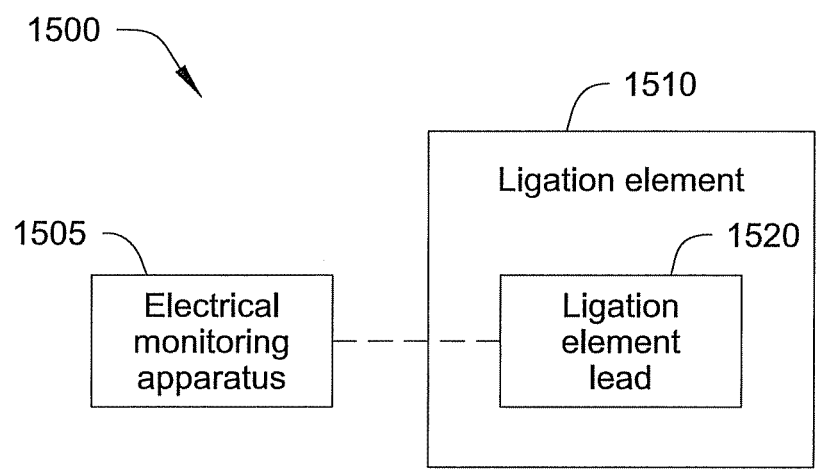

FIG. 25 depicts a portion of another occlusion control system 1500. The system 1500 may include a ligation element 1510 for ligating body tissue (e.g., the ligation element 1510 may include a loop); a ligation element lead 1520 extending from a first end to a second end and throughout the ligation element 1510; and electrical monitoring apparatus 1505 operably coupled to the first end and the second end of ligation element lead 1520.

The ligation element 1510 may include a wire snare, a hollow suture (e.g., a soft pliable suture having a hollow core within which a more rigid, removable control element extends—as described in, e.g., International Publication WO 2008/036408 titled DEVICES AND METHODS FOR LIGATING ANATOMICAL STRUCTURES), band, elastic, etc. The ligation element 1510 may be formed of, e.g., a monofilament and/or braided suture and may include materials such as, e.g., polyester, PTFE, polyethylene, nylon, polypropylene, metal, and/or any other suitable material used in surgical applications as known by one having ordinary skill in the art. Further, the material of the ligation element 1510 may be absorbable (e.g., material that may break-down within a body without intervention) or non-absorbable. In at least one embodiment, the ligation element 1510 may include shape memory materials such as, e.g., Nitinol.

The ligation element 1510 includes a ligation element lead 1520, e.g., located within the body of the ligation element 1510. The ligation element lead 1520 may be formed of any suitable conductive material, e.g., platinum, copper, gold, iridium, titanium, metal alloys, polymers including conductive materials, etc. As the ligation element 1510 is tightened, e.g., around body tissue (e.g., the LAA), the strain on the lead 1520 may increase. In turn, the intrinsic electrical properties of the ligation element lead 1520 (e.g., resistance, capacitance, impedance, etc.) may change as a result of the strain on the lead 1520. Those changes may be used to provide an indicator as to the forces being exerted on the tissue being ligated. For example, it may be determined that when impedance reaches a threshold value, the force applied on the ligation element lead 1520 is at a particular value. Additionally, any of these electrical measurements of the ligation elements lead could be correlated with other techniques for force/occlusion control described herein to reduce the likelihood of over-tightening of the ligation element.

Multiple electrodes as depicted in the embodiments of FIGS. 26 and 27 may, in some embodiments, bridge the ostium of the left atrial appendage with the most medial electrodes being medial to the ostium and other electrodes on the body of the appendage itself. When ligating the signals (e.g., electrograms) that are medial to the site of ligature will typically remain normal. In contrast, the signals obtained from electrodes located laterally to the place where the ligature is actually being applied may typically decrease in amplitude, decrease in slew rate, and exhibit changes in pacing thresholds and impedance. In a system configured to compare the different signals, a correlation may be made between the signal(s) obtained on the appendage and a reference signal obtained as discussed herein.

Using multiple electrodes may also facilitate validation of the received signal. For example, the medial electrodes over an appendage can, in some embodiments, be used for pacing, thus providing a system configured to verify that the signals obtained by the capture device are atrial signals. Conduction delay from the medial electrodes to the capture device electrodes may be expected to occur as the ligature is being applied and may be a sign that it, in fact, the appendage is located between the two sets of electrodes (i.e., the electrodes on the ligation element and the electrodes on the capture device).

Further, the changing electrical properties of the ligation element lead may be used to control an actuation apparatus 1340 as described herein with reference to FIG. 23. In at least one embodiment, the actuation apparatus (not shown) may be operably coupled to the ligation element to restrict the amount of force/pressure applied by the ligation element to the body tissue by controlling the actuation apparatus itself.

In some embodiments, the electrical monitoring apparatus 1505 may be configured to monitor an impedance of the ligation element lead 1520 and report the impedance to a user. In at least one embodiment, the electrical monitoring apparatus 1505 may be configured to report the amount of tension within the ligation element 1510 based on the monitored impedance. Further, in at least another embodiment, the electrical monitoring apparatus 1505 may be further configured to compare the monitored impedance to a threshold value and determine whether the body tissue has been ligated based on the comparison between the monitored impedance and a threshold value.

The system depicted in FIG. 26 includes a ligation element 1680 that may include one or more electrodes 1682 carried on the ligation element 1380. The ligation element 1680 can be delivered through a delivery device 1610 and the ends of the ligation element can be manipulated to adjust the size of the loop fowled by the ligation element 1680. The electrodes 1682 may preferably be operably connected to one or more leads that extend proximally back through the ligation element 1680 to connect to monitoring apparatus as described herein. Similar devices (not including electrodes) may be described in more detail in U.S. Patent Application Publication No. 2008/0294175 to Bardsley et al.

The system depicted in FIG. 27 includes a ligation element 1780 that may include one or more electrodes 1782 carried on the ligation element 1780. The ligation element 1780 can also be delivered through a delivery device 1710. The electrodes 1782 may preferably be operably connected to one or more leads that extend proximally back through the ligation element 1780 to connect to monitoring apparatus as described herein. Similar devices (not including electrodes) may be described in more detail in U.S. Patent Application Publication No. 2008/0294175 to Bardsley et al.

Although some illustrative capture devices and ligation elements are described herein, many other capture devices and/or ligation elements may be used in the systems and methods described herein. Examples of some potentially useful capture devices and/or ligation elements that may be used in connection with the systems and methods described herein may be found in, e.g., PCT Application Serial No. US2009/38544, filed Mar. 27, 2009, entitled NAVIGATION AND TISSUE CAPTURE SYSTEMS AND METHODS. Additional devices and/or ligation elements may be found in, e.g., U.S. Patent Application Publication No. 2008/0294175 (Bardsley et al.); U.S. Pat. No. 6,488,689 (Kaplan et al.); U.S. Pat. No. 5,865,791 (Whayne et al.); International Publication WO 2008/036408 A2, titled DEVICES AND METHODS FOR LIGATING ANATOMICAL STRUCTURES; US Patent Application Publication No. US 2009/0157118 (Miller et al.); US Patent Application Publication No. US 2009/0143791 (Miller et al.); US Patent Application Publication No. US 2008/0221593 (Liddicoat et al.); US Patent Application Publication No. US 2007/0073313 (Liddicoat et al.); US Patent Application Publication No. US 2008/0147097 (Liddicoat et al.); U.S. Patent Application Publication No. 2008/0294175 (Bardsley et al.); etc.

Among variations that may or may not be explicitly described herein, the following features, components, etc. may be included in the systems described herein. For example, although the devices are depicted as having substantially straight bodies, they may be precurved such that in the absence of an intervening force, the bodies take on a curved shape.

The systems and methods described herein could be used to detect tissues other than the left atrial appendage using other detectable physiological electrical activity that can provide guidance for navigation.

The systems and methods described herein may be used in a manual operation, i.e., where one or more operators manually position the devices described herein. Alternatively, some or all of the devices in the systems and methods described herein may be controlled by automated equipment (e.g., robotically, etc.).

The systems and methods described herein could be used in conjunction with the following surgical techniques: percutaneous, minimally invasive, laparascopic, keyhole, Natural Orifice Transluminal Endoscopic Surgery (NOTES), open surgery, endoscopic surgery, etc. and combinations of two or more techniques.

Although described in connection with the human anatomy, the systems and methods described herein could be used with any animal (i.e., have use in both human and veterinary applications).

Although not explicitly depicted, the EGM detection can be performed between any two electrodes or between a single electrode and ground (electrically neutral). Ground can be created by, e.g., placing a patch electrode on a subject's body (or placing another electrode on or on the body) and using it as a reference electrode.

The complete disclosure of the patents, patent documents, and publications cited herein are incorporated by reference in their entirety as if each were individually incorporated.

Exemplary embodiments of navigation and tissue capture systems and methods have been discussed and reference has been made to possible variations. These and other variations and modifications will be apparent to those skilled in the art without departing from the scope of the invention, and it should be understood that the invention is not limited to the illustrative embodiments set forth herein. Accordingly, the invention is to be limited only by the claims provided below and equivalents thereof.

The invention claimed is:

1. A tissue capture system comprising:
   a capture device configured to capture body tissue;
   a capture shaft comprising an elongated body comprising a proximal end and a distal end, wherein the distal end of the capture shaft is coupled to the capture device;
   a first capture device electrode coupled to the capture device;
   a second capture device electrode coupled to the capture device; and
   electrical monitoring apparatus operably coupled to the first capture device electrode and the second capture device electrode, wherein the electrical monitoring apparatus is configured to:
   monitor an impedance between the first capture device electrode and the second capture device electrode; and
   determine whether the capture device has captured atrial tissue based on the monitored impedance.

2. A system according to claim 1, wherein the capture device comprises a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration, and wherein the first capture device electrode is coupled to the interior surface of the first jaw and the second capture device electrode is coupled to the interior surface of the second jaw.

3. A system according to claim 1, wherein the capture device comprises a first jaw and a second jaw, wherein the first jaw and the second jaw comprise an open configuration in which the first jaw and the second jaw are open and a closed configuration in which the first jaw and the second jaw are closed, wherein an interior surface of the first jaw is located closer to an interior surface of the second jaw when the first jaw and the second jaw are in the closed configuration than when the first jaw and the second jaw are in the open configuration, and wherein the first capture device electrode is coupled to the interior surface of the first jaw and wherein the interior surface of the second jaw is free of any electrodes.

4. A system according to claim 1, wherein the system further comprises force-limiting apparatus operably coupled to the capture device to restrict the amount of force applied by the capture device to the body tissue, wherein the electrical monitoring apparatus is further operably coupled to the force-limiting apparatus and is further configured to use the force-limiting apparatus to restrict the amount of force applied by the capture device based on the monitored impedance.

5. A system according to claim 1, wherein the electrical monitoring apparatus is further configured to monitor the impedance between the first capture device electrode and the second capture device electrode by monitoring the impedance at a selected amplitude between the first capture device electrode and the second capture device electrode.

6. A system according to claim 1, wherein the electrical monitoring apparatus is configured to determine whether the capture device is proximate atrial tissue based on the monitored impedance by comparing the monitored impedance to a threshold value.

7. A system according to claim 1, wherein the electrical monitoring apparatus is further configured to provide an indication to restrict the amount of force applied by the capture device based on the monitored impedance.

8. A system according to claim 1, wherein the electrical monitoring apparatus is further configured to determine whether the capture device has captured atrial tissue based on change in the monitored impedance.

9. A tissue capture system comprising:
   a capture device configured to capture body tissue;
   a capture shaft comprising an elongated body comprising a proximal end and a distal end, wherein the distal end of the capture shaft is coupled to the capture device;
   a ligation element comprising a loop, wherein the ligation element is configured to ligate the body tissue by tightening of the loop around the body tissue; and
   force-limiting apparatus operably coupled to the ligation element to restrict the amount of force applied by ligation element when the ligation element is tightened around the body tissue.

10. A system according to claim 9 further comprising a force-limiting apparatus operably coupled to the capture device to restrict the amount of force applied by the capture device to the body tissue.

11. A tissue capture system comprising:
    a capture device configured to capture body tissue;
    a capture shaft comprising an elongated body comprising a proximal end and a distal end, wherein the distal end of the capture shaft is coupled to the capture device;
    an electrode coupled to the capture device;
    a ligation element configured to ligate the body tissue;
    force-limiting apparatus operably coupled to the ligation element to restrict the amount of force applied by ligation element when the ligation element is tightened around the body tissue; and
    electrical monitoring apparatus operably coupled to the electrode, wherein the electrical monitoring apparatus is configured to:
    monitor electrical activity of the body tissue using the electrode;
    compare the monitored electrical activity to a threshold value;
    determine whether the body tissue has been ligated based on the comparison between the monitored electrical activity and the threshold value; and
    use the force-limiting apparatus to restrict the amount of force applied by the ligation element based on the comparison between the monitored electrical activity and the threshold value.

12. A system according to claim 11, wherein the force-limiting apparatus comprises a spring operably coupled to the ligation element.

13. A tissue capture system comprising:
    a capture device configured to capture body tissue;
    a capture shaft comprising an elongated body comprising a proximal end and a distal end, wherein the distal end of the capture shaft is coupled to the capture device;
    an electrode coupled to the capture device;
    actuation apparatus operably coupled to the capture device and configured to actuate the capture device to capture the body tissue;

a ligation element configured to ligate the body tissue; and electrical monitoring apparatus operably coupled to the electrode and the actuation apparatus, wherein the electrical monitoring apparatus is configured to:

monitor electrical activity of the body tissue using the electrode;

compare the monitored electrical activity to a threshold value; and determine whether the body tissue has been ligated based on the based on the comparison between the monitored electrical activity and the threshold value; and actuate the capture device to capture the body tissue using the actuation apparatus based on the monitored electrical activity.

14. A tissue capture system comprising:

a capture device configured to capture body tissue;

a capture shaft comprising an elongated body comprising a proximal end and a distal end, wherein the distal end of the capture shaft is coupled to the capture device;

an electrode coupled to the capture device;

a ligation element configured to ligate the body tissue;

actuation apparatus operably coupled to the ligation element to tighten and loosen the ligation element around the body tissue; and electrical monitoring apparatus operably coupled to the electrode and the actuation apparatus, wherein the electrical monitoring apparatus is configured to:

monitor electrical activity of the body tissue using the electrode;

compare the monitored electrical activity to a threshold value; and determine whether the body tissue has been ligated based on the based on the comparison between the monitored electrical activity and the threshold value; and tighten the ligation element around the body tissue using the actuation apparatus based on the monitored electrical activity.

15. A tissue capture system comprising:

a capture device configured to capture body tissue;

a capture shaft comprising an elongated body comprising a proximal end and a distal end, wherein the distal end of the capture shaft is coupled to the capture device;

an electrode coupled to the capture device;

a ligation element comprising a loop, wherein the ligation element is configured to ligate the body tissue by tightening of the loop around the body tissue; and electrical monitoring apparatus operably coupled to the electrode, wherein the electrical monitoring apparatus is configured to:

monitor electrical activity of the body tissue using the electrode;

compare the monitored electrical activity to a threshold value; and determine whether the body tissue has been ligated based on the based on the comparison between the monitored electrical activity and the threshold value after tightening of the loop around the body tissue.

16. A system according to claim 15, wherein the electrical monitoring apparatus is further configured to obtain the threshold value using the electrode coupled to the capture device.

17. A system according to claim 15, wherein the electrical activity monitored by the electrical monitoring apparatus is impedance and the electrical monitoring apparatus is further configured to determine that sufficient occlusion of the body tissue has occurred after detecting a selected increase in the impedance of the body tissue.

18. A system according to claim 15, wherein the electrical activity monitored by the electrical monitoring apparatus is impedance; and wherein the electrical monitoring apparatus is configured to obtain the threshold value using the electrode coupled to the capture device; and further wherein the electrical monitoring apparatus is configured to determine that sufficient occlusion of the body tissue has occurred after detecting a selected increase in the impedance of the body tissue.

19. A system according to claim 15, wherein the electrical activity monitored by the electrical monitoring apparatus comprises an EGM signal and the electrical monitoring apparatus is further configured to determine that sufficient occlusion of the body tissue has occurred after detecting a selected decrease in the EGM signal of the body tissue.

20. A system according to claim 15, wherein the electrical activity monitored by the electrical monitoring apparatus comprises an EGM signal and the electrical monitoring apparatus is further configured to determine that sufficient occlusion of the body tissue has occurred after detecting a selected increase in pacing capture threshold of the body tissue.

* * * * *